United States Patent
Röder et al.

(10) Patent No.: US 9,279,798 B2
(45) Date of Patent: Mar. 8, 2016

(54) DEEP-MALDI TOF MASS SPECTROMETRY OF COMPLEX BIOLOGICAL SAMPLES, E.G., SERUM, AND USES THEREOF

(71) Applicant: Biodesix, Inc., Boulder, CO (US)

(72) Inventors: Heinrich Röder, Steamboat Springs, CO (US); Senait Asmellash, Denver, CO (US); Jenna Allen, Louisville, CO (US); Maxim Tsypin, Steamboat Springs, CO (US)

(73) Assignee: Biodesix, Inc., Boulder, CO (US)

( * ) Notice: Subject to any disclaimer, the term of this patent is extended or adjusted under 35 U.S.C. 154(b) by 0 days.

(21) Appl. No.: 13/836,436

(22) Filed: Mar. 15, 2013

(65) Prior Publication Data

US 2013/0320203 A1    Dec. 5, 2013

Related U.S. Application Data

(60) Provisional application No. 61/652,394, filed on May 29, 2012.

(51) Int. Cl.
| | |
|---|---|
| G01N 33/487 | (2006.01) |
| H01J 49/16 | (2006.01) |
| G01N 33/68 | (2006.01) |
| H01J 49/00 | (2006.01) |
| H01J 27/24 | (2006.01) |
| H01J 49/40 | (2006.01) |

(52) U.S. Cl.
CPC .......... *G01N 33/487* (2013.01); *G01N 33/6851* (2013.01); *H01J 49/0004* (2013.01); *H01J 49/164* (2013.01)

(58) Field of Classification Search
CPC . G01N 33/487; G01N 33/6851; H01J 49/164; H01J 49/0004
USPC ......................................... 250/282, 287, 424
See application file for complete search history.

(56) References Cited

U.S. PATENT DOCUMENTS

| | | | |
|---|---|---|---|
| 7,109,491 | B2 | 9/2006 | Shinden |
| 7,736,905 | B2 | 6/2010 | Roder et al. |

(Continued)

OTHER PUBLICATIONS

Asperger, A., et al. "A new high capacity MALDI target format facilitating improved LC-MALDA analysis of complex proteomics samples" HUPO, pp. 256 (2011).*

(Continued)

*Primary Examiner* — Robert Kim
*Assistant Examiner* — Wyatt Stoffa
(74) *Attorney, Agent, or Firm* — McDonnell Boehnen Hulbert & Berghoff LLP

(57) ABSTRACT

A method of analyzing a biological sample, for example serum or other blood-based samples, using a MALDI-TOF mass spectrometer instrument is described. The method includes the steps of applying the sample to a sample spot on a MALDI-TOF sample plate and directing more than 20,000 laser shots to the sample at the sample spot and collecting mass-spectral data from the instrument. In some embodiments at least 100,000 laser shots and even 500,000 shots are directed onto the sample. It has been discovered that this approach, referred to as "deep-MALDI", leads to a reduction in the noise level in the mass spectra and that a significant amount of additional spectral information can be obtained from the sample. Moreover, peaks visible at lower number of shots become better defined and allow for more reliable comparisons between samples.

21 Claims, 13 Drawing Sheets

(56) References Cited

U.S. PATENT DOCUMENTS

| | | | |
|---|---|---|---|
| 7,989,762 B2* | 8/2011 | Holle et al. | 250/288 |
| 8,467,988 B1* | 6/2013 | Roder et al. | 702/116 |
| 2002/0158196 A1 | 10/2002 | Berggren | |
| 2004/0038423 A1* | 2/2004 | Smirnov et al. | 436/173 |
| 2004/0183006 A1* | 9/2004 | Reilly et al. | 250/282 |
| 2004/0183009 A1* | 9/2004 | Reilly et al. | 250/288 |
| 2004/0191249 A1* | 9/2004 | Hallahan et al. | 424/141.1 |
| 2004/0214338 A1* | 10/2004 | Borchers | 436/86 |
| 2004/0262514 A1* | 12/2004 | Lennon et al. | 250/288 |
| 2005/0236564 A1 | 10/2005 | Keller | |
| 2006/0214104 A1* | 9/2006 | Pope et al. | 250/297 |
| 2006/0247863 A1* | 11/2006 | Bui | 702/19 |
| 2007/0178541 A1* | 8/2007 | Pedersen et al. | 435/7.32 |
| 2007/0278400 A1* | 12/2007 | Schurenberg et al. | 250/288 |
| 2008/0290271 A1* | 11/2008 | Togashi | 250/288 |
| 2008/0318332 A1* | 12/2008 | Mechref et al. | 436/106 |
| 2009/0039282 A1 | 2/2009 | Haase | |
| 2009/0208921 A1* | 8/2009 | Tempst et al. | 435/4 |
| 2010/0044563 A1* | 2/2010 | Harada et al. | 250/288 |
| 2010/0057372 A1* | 3/2010 | Fagerquist et al. | 702/20 |
| 2010/0187475 A1* | 7/2010 | Pope et al. | 252/184 |
| 2010/0237238 A1* | 9/2010 | Franzen | 250/283 |
| 2011/0056311 A1* | 3/2011 | DiCesare | 73/863.21 |
| 2011/0065207 A1* | 3/2011 | Ferrari et al. | 436/501 |
| 2011/0070659 A1* | 3/2011 | Belisle et al. | 436/501 |
| 2011/0136166 A1* | 6/2011 | Semmes et al. | 435/40.52 |
| 2011/0268744 A1* | 11/2011 | Garthwaite et al. | 424/158.1 |
| 2011/0315930 A1* | 12/2011 | Pope et al. | 252/364 |
| 2012/0074308 A1* | 3/2012 | Urbani et al. | 250/282 |
| 2012/0165246 A1* | 6/2012 | Lindner et al. | 514/2.4 |
| 2012/0205592 A1* | 8/2012 | Hajivandi et al. | 252/408.1 |
| 2012/0326019 A1* | 12/2012 | Claude et al. | 250/282 |
| 2013/0056628 A1* | 3/2013 | Holle et al. | 250/282 |
| 2013/0146758 A1* | 6/2013 | Urban et al. | 250/281 |
| 2014/0206094 A1* | 7/2014 | Amano et al. | 436/94 |

OTHER PUBLICATIONS

Keller, B. et al. "Discerning Matrix-Cluster Peaks in Matrix-Assisted Laser Desorption/Ionization Time-of-Flight Mass Spectra of Dilute Peptide Mixtures" J Am Soc Mass Spectrum 2000, 11, 88-9.*

Albrethsen, J., "The first decade of MALDI protein profiling: A lesson in translational biomarker research", Journal of Proteomics, 74:765-773 (2011).

Hortin, G., "The MALDI-TOF Mass Spectrometric View of the Plasma Proteome and Peptidome", Clinical Chemistry, 52:1223-1237 (2006).

Leszyk, J., "Evaluation of the New MALDI Matrix-4-Chloro-α-Cyanocinnamic Acid", Journal of Biomolecular Techniques, 21:81-91 (2010).

Zhang, et al., "Effects of common surfactants on protein digestion and matrix-assisted laser desorption/ionization mass spectrometric analysis of the digested peptides using two-layer sample preparation", Rapid Communications in Mass Spectrometry, 18:889-896 (2004).

International Search Report for corresponding PCT application No. PCT/US13/031998, dated Dec. 11, 2014.

flexControl User Manual, 2006, XP055235014, Retrieved from the Internet: URL:http://www.biomolar.uottawa.ca/MALDI_Info_files/flexControl_User_Manual.pdf [retrieved on Dec. 9, 2015].

European Search Report for corresponding European application No. 13713042.3, dated Dec. 16, 2015.

* cited by examiner

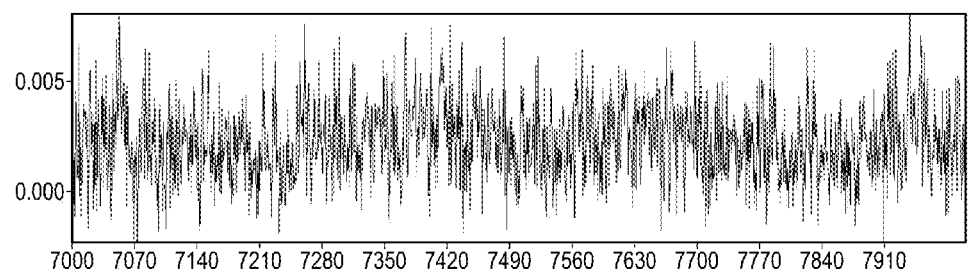
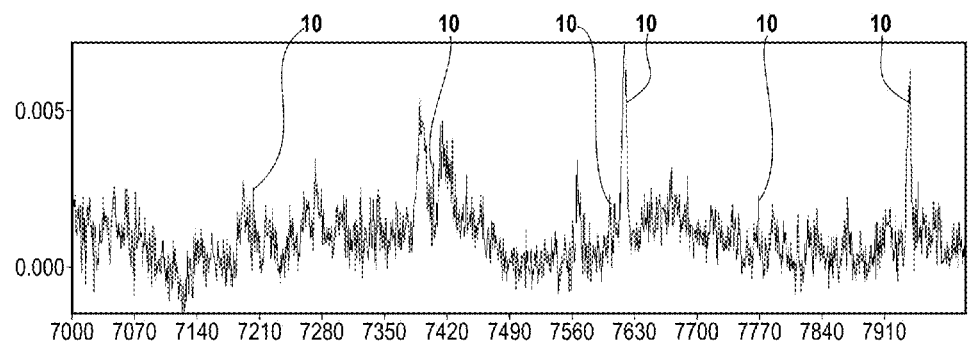
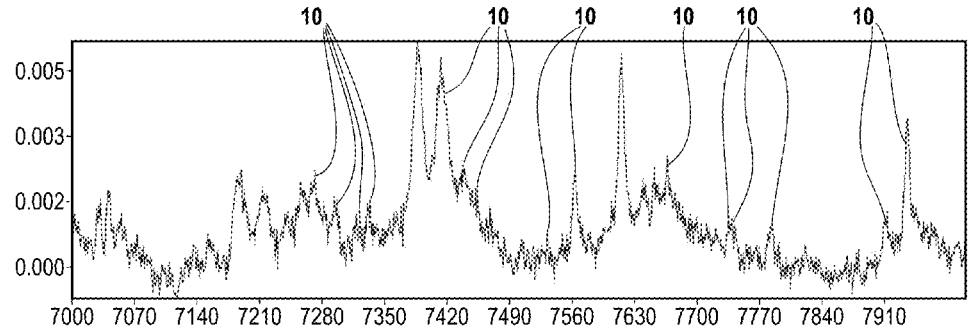

DEEP-MALDI TOF MASS SPECTROMETRY OF COMPLEX BIOLOGICAL SAMPLES, E.G., SERUM, AND USES THEREOF

CROSS-REFERENCE TO RELATED APPLICATION

This application claims priority benefits under 35 U.S.C. §119 to U.S. provisional application Ser. No. 61/652,394 filed May 29, 2012, the content of which is incorporated by reference herein.

BACKGROUND

This disclosure relates to the fields of mass spectrometry, biomarker discovery, assay development, and clinical testing.

CURRENT TECHNOLOGY

In MALDI (matrix assisted laser desorption ionization) TOF (time-of-flight) mass spectrometry, a sample/matrix mixture is placed on a defined location ("spot", or "sample spot" herein) on a metal plate, known as a MALDI plate. A laser beam is directed onto a location on the spot for a very brief instant (known as a "shot"), causing desorption and ionization of molecules or other components of the sample. The sample components "fly" to an ion detector. The instrument measures mass to charge ratio (m/z) and relative intensity of the components (molecules) in the sample in the form of a mass spectrum.

Typically, in a MALDI-TOF measurement, there are several hundred shots applied to each spot on the MALDI plate and the resulting spectra (one per shot) are summed or averaged to produce an overall mass spectrum for each spot. U.S. Pat. No. 7,109,491 discloses representative MALDI plates used in MALDI-TOF mass spectrometry. The plates include a multitude of individual locations or spots where the sample is applied to the plate, typically arranged in an array of perhaps several hundred such spots.

The conventional wisdom, at least in the area of mass spectrometry of complex biological samples such as serum and plasma, is that there is no need to subject the sample to more than roughly 1,000 shots, otherwise the protein content is depleted, the laser and detector in the instrument are subject to undue wear, and furthermore that additional shots would not reveal a significant amount of additional information regarding the sample. Hence, it is common to use 500-1000 shots per sample spot when obtaining mass spectrometry data from complex biological samples, e.g., during biomarker discovery research.

The number of detectable proteins in standard MALDI-TOF MS of serum or plasma is believed to be limited by the large dynamic range of abundance of proteins in circulation. (Horan G. L., The MALDI-TOF mass spectrometric view of the plasma proteome and peptidome. Clin. Chem. 2006; 52:1223-37). Hence it is commonly believed that MALDI-TOF MS of serum is only possible for high abundance proteins in the range of micromoles per liter. This is counter to the observation that MALDI-TOF mass spectrometry can be a very sensitive technique to detect even trace amounts in purified samples. (Albrethsen J. The first decade of MALDI Protein profiling: A lesson in translational biomarker research. J. Proteomics 2011 74: 765-73). This patent application explains this discrepancy and provides methodology to extend the high sensitivity of MALDI-TOF MS from simple samples to complex biological samples such as serum or plasma.

U.S. Pat. No. 7,736,905, assigned to the assignee of the present invention, describes among other things methods for peak identification, spectral alignment, normalization and other pre-processing techniques for mass spectra of biological (e.g., serum) samples and uses thereof in predicting patient response to administration of anti-cancer drugs. The '905 patent is incorporated by reference herein in its entirety.

SUMMARY

In recent exploratory studies, the present inventors have discovered that collecting and averaging many (more than 20,000, and typically 100,000 to 500,000) shots from the same MALDI spot or from the combination of accumulated spectra from multiple spots of the same sample, leads to a reduction in the relative level of noise vs. signal and that significant amount of additional spectral information from mass spectrometry of complex biological samples is revealed. Moreover, a variety of standard paradigms using MALDI TOF MS appear to be plain wrong. First, it is possible to run hundreds of thousands of shots on a single spot before the protein content on the spot is completely depleted. Second, the reduction of noise via averaging many shots leads to the appearance of previously invisible peaks (i.e., peaks not apparent at 1,000 shots). Third, even previously visible peaks become better defined and allow for more reliable measurements of peak intensity and comparisons between samples when the sample is subject to a very large number of shots (much more than 1,000).

As an example, the present inventors have made the surprising discovery that when a serum or other blood-based sample is subject to MALDI-TOF at greater than 20,000 shots per spot, and typically 250,000 or more shots per spot, and even 2,800,000 shots using multiple MALDI spots, each experiment shows that the protein content of the spot was not rendered unusable. It was further discovered that a very significant amount of spectral information (peaks) is contained in the spectra obtained at these numbers of shots, which are not revealed when the sample is subject to the typical 500 or 1,000 shots. The peaks revealed at, for example, 200,000 shots are believed to correspond to minute quantities of intact (undigested) proteins present in the serum sample. Using the techniques described herein and what is referred to herein as the "deep-MALDI" approach (i.e., greater than 20,000 shots per spot, and preferably roughly 250,000 to 750,000 or more shots from the same spot or from the combination of multiple spots), it is believed that a very large number of proteins, and possibly at least half of all the proteins present in a serum sample, can be detected in a semi-quantitative and reproducible fashion. The detection in a semi-quantitative fashion means that the measurements of intensity (peak height, area under the peak) are related to the absolute abundance or concentration of the proteins in the sample. The detection in a reproducible fashion means that one can measure the same sample many times and one obtains the same results within some acceptable coefficient of variation.

Obtaining more than 20,000 shots from a single MALDI spot can exceed the parameters of a modern MALDI-TOF machine; however we describe in this document several methods of working around this limitation. Ideally, the MALDI-TOF instrument is designed to accommodate the "deep-MALDI" approach described in this document, and several specific proposals for such a machine are offered in the following description, including automated raster scanning features and capability of performing vastly more shots on a single spot.

The most pressing issue using many hundreds of thousands of shots from a MALDI sample spot is that in common spot preparation only some shot locations within a spot yield sufficient ion current to contribute substantially to signal in a combined spectrum. While initial results have been obtained using a labor intensive manual process to visually select high ion yield locations within a given spot on a MALDI plate for laser shots, and it is possible to proceed with this approach, automation of the process to select locations for laser shots is possible and preferred for a high throughput implementation of the invention (if not for the simple reason to not waste too many laser shots and degrade the laser life time substantially). An alternative approach is to improve the quality of MALDI spots in such a way that most randomly selected locations yield a high ion current. Both approaches are useful in the generation of deep-MALDI spectra.

Several methods for automation of spectral acquisition are described in this document. Automation of the acquisition may include defining optimal movement patterns of the laser scanning of the spot in a raster fashion, and generation of a specified sequence for multiple raster scans at discrete X/Y coordinate locations within a spot to result in say 750,000 or 3,000,000 shots from one or more spots. For example, spectra acquired from 250,000 shots per each of four sample spots can be combined into a 1,000,000 shot spectrum. As mentioned previously, hundreds of thousands of shots to millions of shots collected on multiple spots containing the same sample can be averaged together to create one spectrum. One method of automation involves the generation of raster files for non-contiguous X/Y raster scanning of a sample spot. Another method involves dividing the spot into a grid of sub-spots (e.g., a 3×3 or 5×5 grid) and generating raster files for raster scanning at discrete X/Y coordinate locations of the sub-spots. A third method is disclosed using image analysis techniques to identify areas of interest containing relatively high concentrations of sample material for spectral acquisition (multiple shots) and/or those areas where the protein concentration is relatively low, and performing spectral acquisition in the areas with relatively high protein concentration.

A further aspect of this disclosure relates to optimizing the process of sample application to the MALDI plate ("spotting") to produce uniform, homogeneous crystals of the sample/matrix within a single spot. This process facilitates obtaining hundreds of thousands of shots from a single spot on the MALDI plate using automated methods.

This discovery and methods of this disclosure has many applications, including biomarker discovery, test development, substance testing, validation of existing tests, and hypothesis generation, e.g., in biomarker discovery efforts. The methods further enhance the potential of "dilute and shoot" methods in mass spectrometry research by its ability to reproducibly quantify the amount of many more proteins in a complex sample in a high throughput fashion, as compared to current methodologies. For example, the methods can be used in testing for doping of sports athletes, drug testing, e.g., for detection of THC analytes, metabolite testing, testing for presence and amount of cancer antigen 125 (CA-125), prostate specific antigen (PSA) or C-reactive protein, and environmental or food testing. Other examples of applications include the development of clinical tests based on the protein content of clinical samples from retrospective samples of patients via correlative studies, and follow-up clinical validation.

Terminology used in this document:

1. The term "transient spectrum" refers to the spectrum obtained from a single packet of laser shots directed to a single location or x/y position (each packet consists of a defined number of shots, e.g., 100, 500, 800 shots, etc.) in a MALDI spot.

2. The term "location spectrum" refers to the cumulative sum of one or more transient spectra while the laser shoots x times at the same location in a MALDI spot.

3. The term "spot spectrum" refers to the sum of all the location spectra acquired during shooting over an entire, single MALDI spot. The spot spectrum can be obtained using solely a summing operation to sum the location spectra, or obtained using a summing operation after performing alignment and/or normalization operations (e.g., total ion current normalization) on the location spectra. The spot spectrum can be typically obtained from 100,000 to 500,000 shots on the MALDI spot. Other options for obtaining the spot spectrum are possible, including a) performing background subtraction and normalization on the location spectra and then summing; b) performing background subtraction and alignment on the location spectra and then summing; c) performing background subtraction, alignment, and normalization of the location spectra and then summing. We have found that the best dynamic range is achieved by total ion current normalization (for details see U.S. Pat. No. 7,736,905) of location spectra and then summing; any background subtraction would be done in the spot spectrum.

4. The term "shot location" refers to a given location where the laser beam intercepts a MALDI spot for shooting. In order to obtain 200,000 or 500,000 shots per MALDI spot the laser beam is directed over the MALDI spot to a multitude (e.g., hundreds) of individual shot locations, e.g., manually, or more preferably in an automated fashion using raster scanning of the laser beam over the spot. As explained below, the raster pattern design is important as it is generally undesirable to shoot immediately adjacent spot locations sequentially. Hence, the raster pattern design sequentially selects shot locations that have some spatial separation and repeats the scanning over the entire MALDI spot in a spatially shifted manner to avoid sequential shooting of immediately adjacent locations in the spot.

5. The term "transient spectrum filtering" refers to a filtering or selection process that is used to either accept or reject a transient spectrum. As an example, in transient spectrum filtering, in order for a transient spectrum to be accepted a minimum number (e.g., 5) of peaks within a predetermined m/z range must be present in the transient spectrum, and the signal to noise ratio in the transient spectrum must be above a specified threshold. Other filtering criteria can also be used, such as the total ion current of a spectrum needs to exceed a certain predefined threshold, or by using exclusion lists or inclusion lists as explained below. The spectrum filtering either accepts or rejects the transient spectrum in whole.

6. As used herein, the term "complex biological samples" is defined as samples containing hundreds or thousands of analytes, e.g., intact proteins, whose abundance is spread over a large dynamic range, typically many orders of magnitude. Examples of such complex biological samples include blood or components thereof (serum or plasma), lymph, ductal fluids, cerebrospinal fluid, and expressed prostatic secretion. Such complex biological samples could also consist of environmental or food samples.

BRIEF DESCRIPTION OF THE DRAWINGS

FIGS. 1A-1C are an illustration of three MALDI mass spectra of the same sample in a selected mass/charge range (m/z ratio 7,000 to 8,000), illustrating the increase in detectable peak content with increasing number of shots. The spectrum of FIG. 1A resulted from 2,000 shots, the spectrum of FIG. 1B resulted from 100,000 shots, and spectrum of FIG. 1C resulted from 500,000 shots. Note how the spectra of FIGS. 1B and 1C, resulting from our methods, reveal a wealth of spectral information on the sample which was not present in the spectrum of FIG. 1A, which appears essentially as noise.

In FIG. 1D, a portion of the spectrum in an m/z range from 7140 to 7890 Da is shown enlarged in the inset of FIG. 1D showing a wealth of spectral information obtained at approximately 500,000 shots. In FIG. 1E, the spectrum is shown in the inset with the Y axis amplified in order to show additional spectral information and peaks in the region of m/z around 9520, which are revealed with the deep-MALDI method but which are not visible in a typical ~1,000 shot spectrum.

DETAILED DESCRIPTION

1. Overview

Figure 1D:
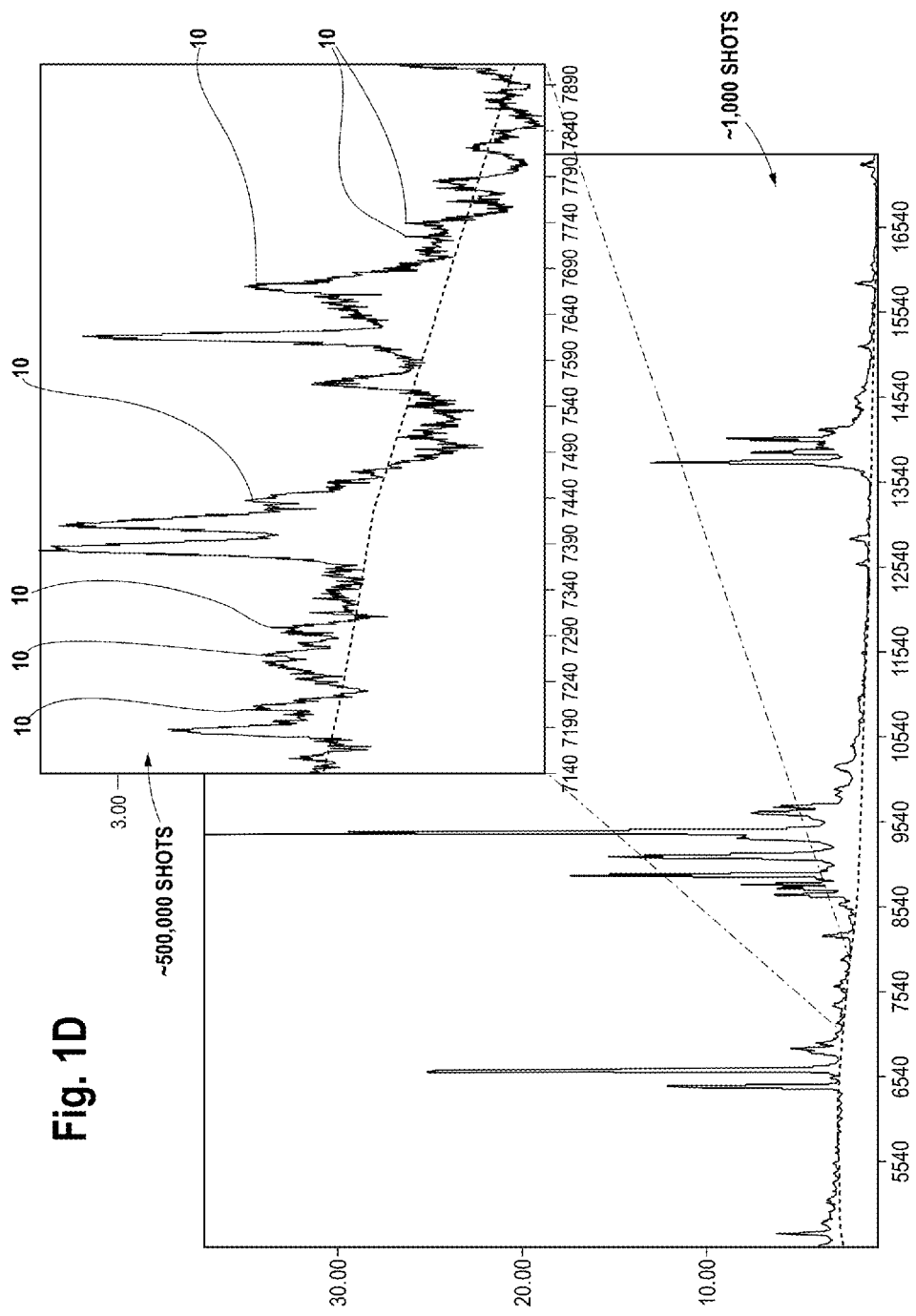
FIGS. 1D and 1E are further examples of mass spectra showing the enormous dynamic range of spectra obtained in our deep-MALDI method.

It has been discovered that subjecting a complex biological sample, such as for example a blood-based sample, to a large number of shots on a single spot (>20,000 and even 100,000 or 500,000 shots) in MALDI-TOF mass spectrometry leads to a reduction in the noise level and the revealing of previously invisible peaks (i.e., peaks not apparent at 2,000 shots). Moreover, this can be done without depletion of the protein content of the sample. Additionally, previously visible peaks become better defined and allow for more reliable comparisons between samples. In standard spectra of blood-based samples (~1,000 shots), typically 60-80 peaks are visible, whereas with 200,000 shots typically ~200-220 peaks are visible, with 500,000 shots typically ~450-480 peaks are visible, and with 2,800,000 shots typically ~760 peaks are visible. It should be understood that the number of peaks reported here is related to MALDI-TOF instrument settings and these numbers are only a rough guide; depending on instrument settings and also on particular peak detection algorithms (and of course the actual sample) more or fewer peaks will be visible. It also must be noted that the quality of peaks and the quantification of intensity (related to abundance) is also better at least under some measure, as is illustrated in FIGS. 1A-1D discussed below.

FIGS. 1A-1C are the plots of a selected mass/charge range (m/z ratio 7,000 to 8,000) showing three spectra of the same sample (serum) illustrating the increase in detectable peak content with increasing number of shots. The spectrum of FIG. 1A resulted from 2,000 shots, the spectrum of FIG. 1B resulted from 100,000 shots, and the spectrum of FIG. 1C resulted from 500,000 shots. Note particularly how the spectrum of FIG. 1A appears essentially as noise and appears to contain little or no discernible spectral information of interest. Contrast FIG. 1A with 1B in which the spectrum of FIG. 1B (spectrum obtained from 100,000 shots) contains many individual peaks, e.g., the peaks identified at 10), that are not present in the spectrum of FIG. 1A. In the spectrum of FIG. 1C, there are many peaks shown in the spectrum that are not shown in the other spectra, or which might have been deemed as noise in the bottom spectrum. Comparing FIGS. 1C and 1B to FIG. 1A, it is apparent that a wealth of spectral information is revealed at 100,000 shots and 500,000 shots that is not present in the spectrum of FIG. 1A (2,000 shots), and that the noise level is reduced by the deep-MALDI method as demonstrated in FIGS. 1B and 1C.

The spectra of FIG. 1B are 1C increase the sensitivity of the spectra to a dynamic range that can be specified and can allow one to correlate peak intensity to abundance. It is possible to use peak intensity to analyze a complex biological sample for presence of a molecule at a given concentration. For example, in this method one would define the molecule of interest (of known mass) in the sample, dope the specimen to a target abundance level (molar concentrations, or ppm) and apply to a MALDI plate; perform a number of shots on the plate (e.g., more than 100,000) until the molecule is reliably present in the spectrum (a peak at a known m/z position) at a particular abundance (intensity), and record the number of shots ("x"). This procedure to generate what is referred to as a "reference spectrum" would be subject to routine qualification and standardization methods to ensure reliability, as would be apparent to persons skilled in the art. Then, a sample of interest for testing would be subject to MALDI-TOF and x number of shots. If the resulting spectrum revealed that the intensity of the peak at the known position corresponding to the molecule of interest was less than the intensity of the peak in the reference spectrum then the concentration of the molecule of interest in the sample is less than the concentration of the molecule in the sample used in generation of the reference spectrum. This approach could be used for multiple analytes simultaneously. Furthermore, multiple reference spectra could be obtained for the molecule of interest over a range of known concentrations at x shots and the test spectrum could be compared to the reference spectra to determine an approximate concentration of the molecule of interest in the test sample. This method can be used for many purposes, e.g., drug testing, e.g., for athletes, testing of metabolite concentration, environmental sample testing, etc. The molecule of interest could be a protein, e.g., metabolite, cancer antigen (CA) 125, prostate-specific antigen (PSA), C-reactive protein, etc., in a mass range of approximately 1K Daltons to 50 K Daltons.

Figure 1E:
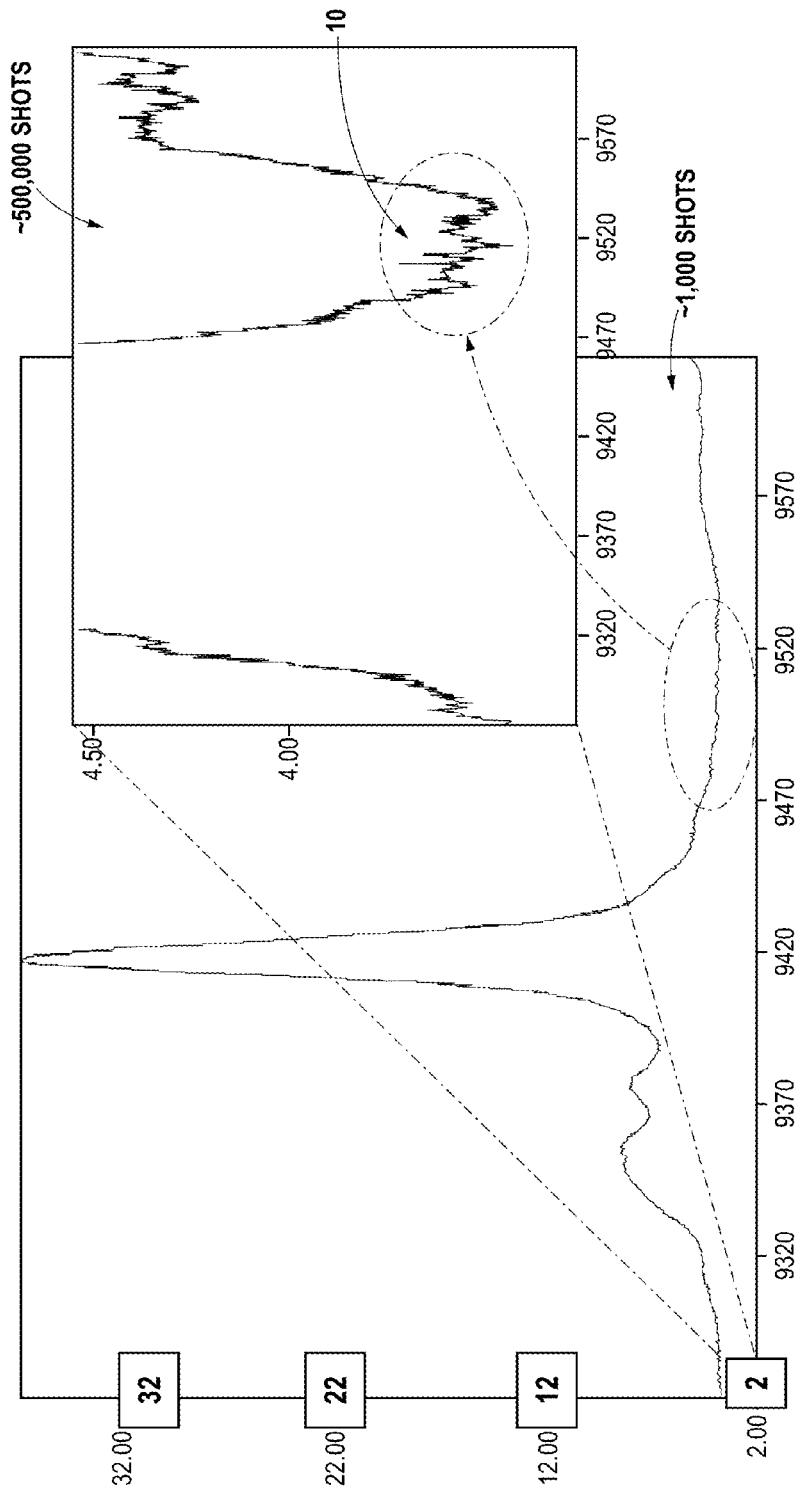

FIG. 1D is an illustration of the enormous dynamic range in a spectrum that is revealed in the deep-MALDI approach. The inset in FIG. 1D is a portion of a spectrum in the m/z range between 7140 kDa and 7890 kDa showing the spectrum, and multitude of peaks 10, obtained at about ~500,000 shots. A background estimate (dashed line) is superimposed over the spectra, which could be subtracted out to produce a background subtracted spectrum. Note that the spectrum information in the inset and in particular many of the peaks 10 are not visible in the main portion of FIG. 1D. In FIG. 1E, the spectrum is shown in the inset with the Y axis amplified in order to show the additional spectral information and in particular intensity information for peaks in the region of m/z around 9520 which are revealed with the deep-MALDI method but which are not visible in a typical ~1,000 shot spectrum.

Figure 2A:
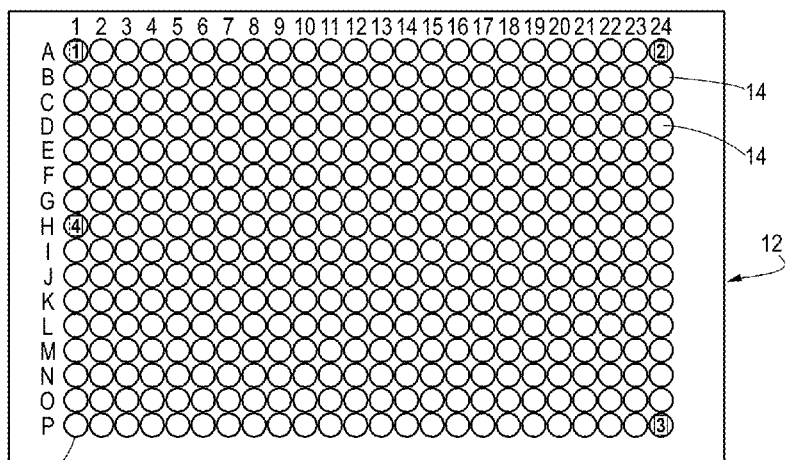
FIG. 2A is a plan view of a MALDI-TOF target plate containing 384 sample spots or "spots" arranged in a rectangular array. The spots are identified by column numbers 1 . . . 24 and rows A . . . P, e.g., the upper left spot is identified as A1.
Figure 2B:
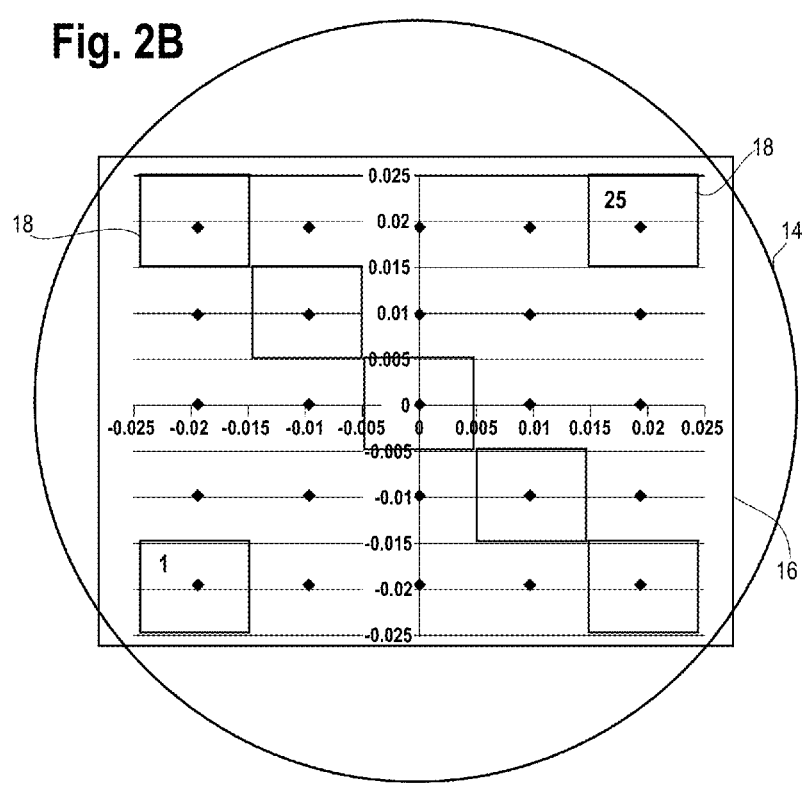
FIG. 2B is an enlarged view of an individual sample spot P1 which is shown divided into a 5×5 rectangular grid having X/Y location coordinates and an origin (0,0) at the center of the spot. The rectangular grid and location coordinates are used in an automated raster scanning approach to acquire spectra from 100,000 or more shots from the spot as described in detail herein.

FIG. 2A is a plan view of a MALDI-TOF target plate 12 containing 384 sample spots or "spots" 14 arranged in a rectangular array. The spots are identified by column numbers 1 ... 24 and rows A ... P, e.g., the upper left spot is identified as A1. FIG. 2B is an enlarged view of an individual sample spot P1 (14) on which is superimposed an X/Y coordinate system 16 having an origin (0,0). The sample spot 14 is shown divided into a 5×5 rectangular grid 25 individual sub-spots 18. The rectangular grids 18 and location coordinate system 16 are used in an automated raster scanning approach to acquire 100,000 or more shots from the spot as described in detail below.

It was initially noted that automated generation of a large number of shots (>20,000) is not absolutely necessary and existing features in currently available MALDI-TOF instruments could be used. In general, in the present deep-MALDI technique, it is important to select locations on a MALDI spot that produce a high protein yield when exposed to a laser shot. The standard software in existing mass spectrometry instruments allows for moving over a spot using regular pre-defined paths, i.e. square pattern, hexagonal pattern, spiral pattern (from the center of a spot). Shot locations on a MALDI plate are defined in a process called 'teaching', a part of the Flex-Control™ (Bruker) mass spec control software present in an existing MALDI-TOF instrument of Bruker Corporation. (While mention is made herein occasionally to features of a Bruker Corporation instrument, the inventive methods are of course not limited to any particular instrument or instruments of a particular manufacturer.)

Figure 3:
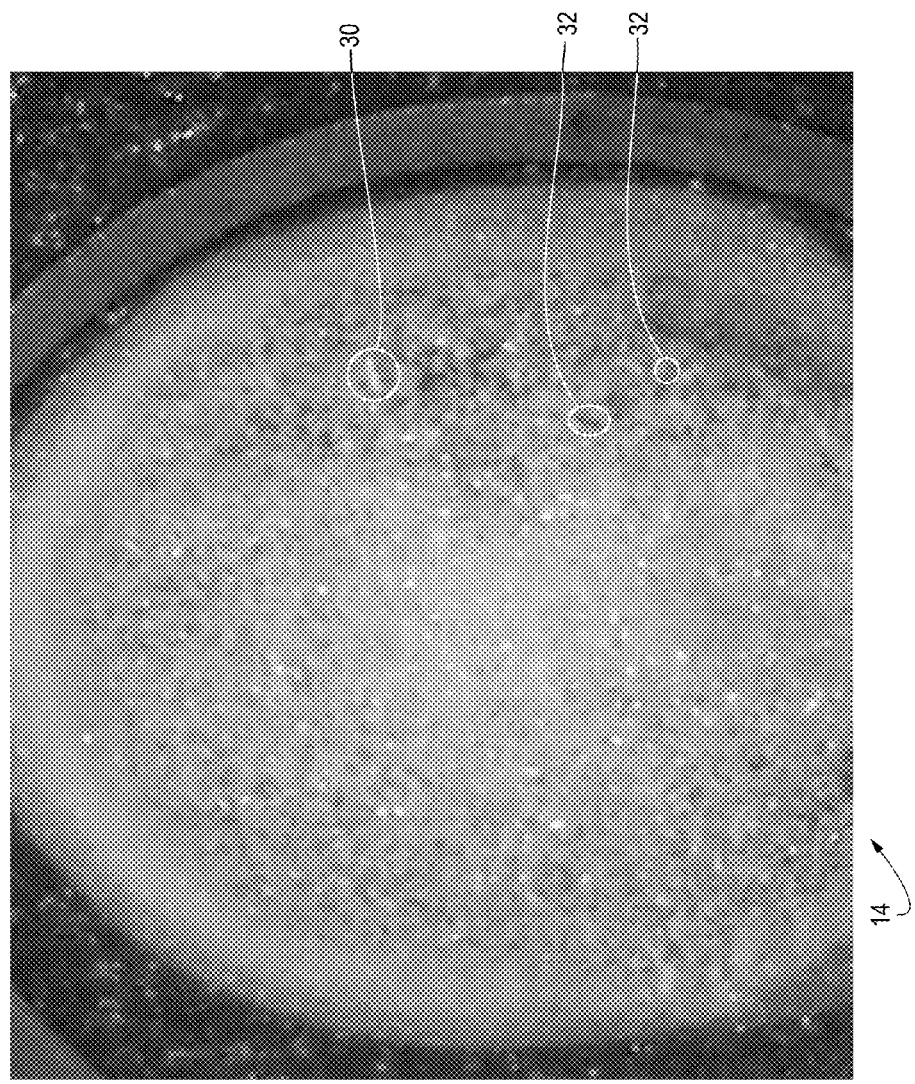
FIG. 3 is a photograph of a biological sample/matrix mixture deposited in a single spot in the MALDI plate of FIG. 2A. Ideally, the spot contains a uniform, homogenous crystallized sample within the spot, as shown in FIG. 3.

An example of a MALDI spot containing a specimen/matrix mixture evenly distributed within the spot is shown in FIG. 3. Mass spectrometry instruments from Bruker Corporation include a built-in camera that shows areas of a MALDI spot; in manual selection one would pick bright locations 30 to aim the laser at. Dark locations 32 should be avoided. Sometimes bright locations do not produce good yields, which may be related to the presence of salt crystals. Over the process of shooting, areas in a spot can become depleted; hence dark areas (depleted areas with low yield) need to be avoided. The manual approach would continue to acquire and display images of the spot over the course of shooting.

In the course of our preliminary experiments we found that it was becoming increasingly harder to find good locations as more and more shots were used. This effect was also seen when the same spot was used repeatedly, e.g. adding a second half million shots following a previous half million shots. The second run did not result in as much a reduction of noise level in mass spectra as was expected. In fact, the resulting averaged spectra may be of worse overall quality, possibly arising from averaging shots from too many empty locations. This might result in an acquisition bias towards early locations if using the eye alone to select shot locations and accept or reject spectra and not using transient spectrum filtering, and such bias needs to be controlled. If one uses automated raster scanning and location spectrum filtering this bias is eliminated.

However, to increase throughput, it is desirable to automate the process of location selection and obtain high numbers of shots from a given spot. Several methods are described in the following section. Methods described below are capable of acquiring 750,000 shots from a sample located on three spots (250,000 shots per spot) in a MALDI plate in 13-15 minutes, with the sample requirement of 3 microliters of serum.

2. Automation of Spectra Collection

While results have been obtained using a labor intensive manual process to visually select locations within a given spot on a MALDI plate for multiple shots to yield 100,000 or 500,000 shots per spot, and it is possible to proceed with this approach, automation of the process to select locations for laser shots is possible and several methods are described in this document.

Automation of the acquisition may include defining optimal movement patterns of the laser scanning of the spot in a raster fashion, and sequence generation for multiple raster scans at discrete X/Y locations within a spot to result in, for example, 100,000, 250,000 or 500,000 shots from the sample spot. One method of automation involves the generation of raster files for non-contiguous X/Y raster scanning of a sample spot. The raster pattern design is important, as it is generally undesirable to shoot immediately adjacent spot locations sequentially. Hence the raster pattern design sequentially selects shot locations that have some spatial separation and repeats the scanning over the entire MALDI spot in a spatially shifted manner to avoid sequential shooting of immediately adjacent locations in the spot and to select new shot locations.

Another method involves dividing the spot into a grid of sub-spots (e.g., a 3×3 or 5×5 grid) (see FIG. 2B) and generating of raster scanning files for raster scanning at discrete X/Y locations of the sub-spots.

A third method is disclosed using image analysis techniques to identify areas of interest containing relatively high concentrations of sample material for spectral acquisition (multiple shots) and/or those areas where the sample (e.g., protein) concentration is relatively low, and avoiding spectral acquisition in areas of relatively low sample (e.g., protein) concentration.

A. Raster scanning of non-contiguous X-Y coordinates

One method of automation of the process of obtaining a large number of shots from a spot involves the generation of raster files for non-contiguous X/Y raster scanning of a sample spot. This will be described in conjunction with FIGS. 4 and 5.

Figure 4:
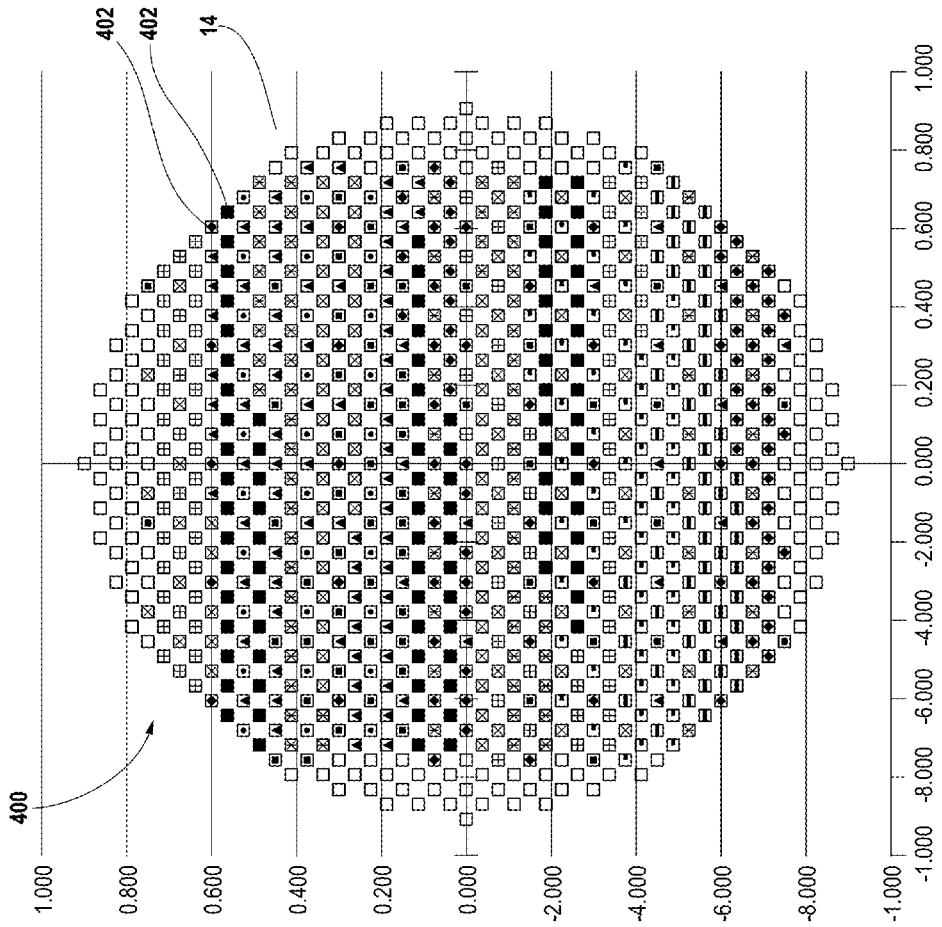
FIG. 4 is an illustration of one possible raster scanning pattern for use in obtaining 100,000 or more shots from the spot of FIG. 3. The spot is raster scanned multiple times, e.g., 25 times. Each symbol set (triangle, square, X, etc.) shown in FIG. 4 depicts a set of individual, discrete X/Y locations where the spot is scanned (shot) in a single raster scan. At each location, the spot can be subject to multiple shots, e.g., 700 or 800 shots.
Figure 5:
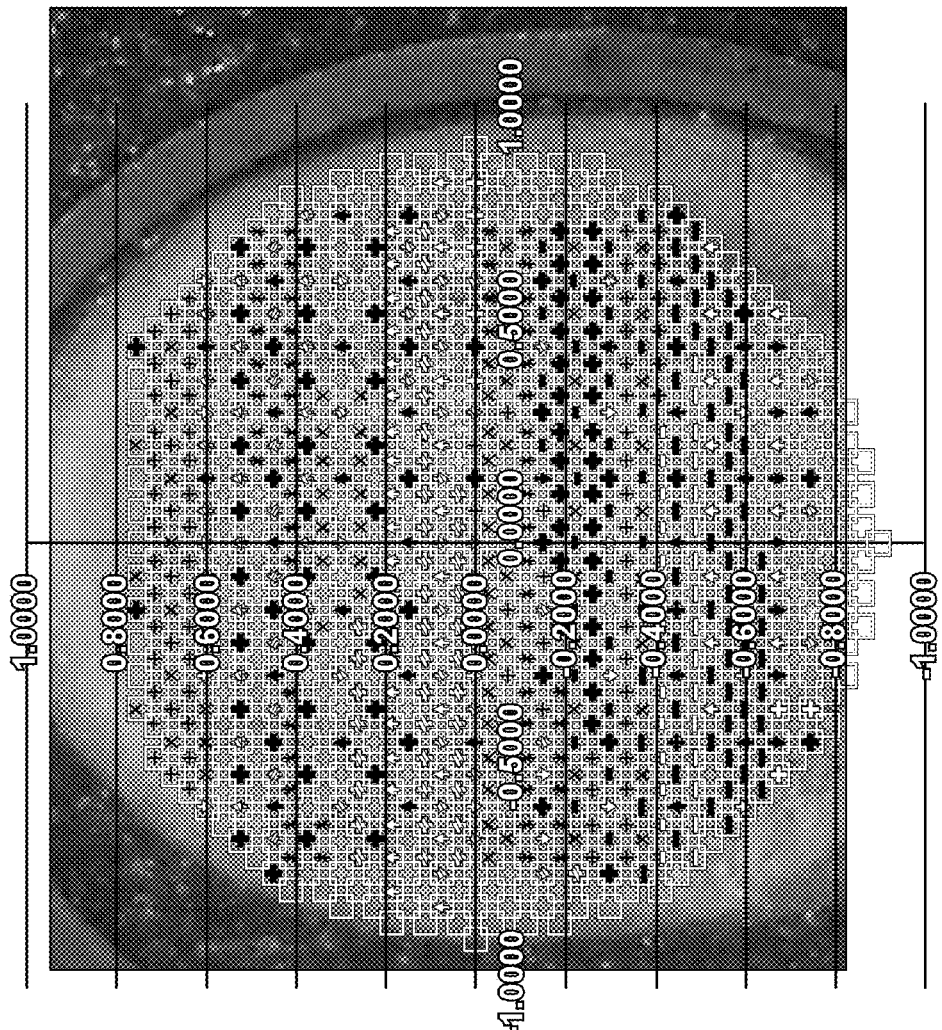
FIG. 5 is an illustration showing the superposition of the raster scanning pattern of FIG. 4 on the sample spot of FIG. 3.

FIG. 4 is an illustration of a raster scanning pattern 400 for use in obtaining 100,000 or more shots from the spot 14 of FIG. 3. The spot 14 is raster scanned multiple times, e.g., 25 times in a sequential fashion. The symbol sets shown in FIG. 4 depict individual, discrete X/Y locations where the spot is scanned (shot) in a single raster scan. The X/Y locations are defined according to a coordinate system shown in the Figure having an origin at the center (position 0,0). During scanning, when the laser is directed to each location, the sample at that location can be subject to a great many shots, e.g., 700 or 800 shots per position/location. One will note from the pattern shown in FIG. 4 that each raster scan consists of shooting at individual, discrete locations within the spot. The individual raster scans are implemented sequentially thereby avoiding shooting immediately adjacent locations in the spot. FIG. 5 shows the superposition of the raster patterns of FIG. 4 over the spot of FIG. 3.

A procedure for generation of 25 raster files with non-contiguous X/Y coordinates for raster scanning as shown in FIG. 4 is described in Appendix 1, which is part of this disclosure.

B. Use of Grids to Separate a Spot into Sub-Spots and Raster Scanning of Sub-Spots An objective of this method is to automate the process of manually selecting locations/rasters on a sample spot (i.e. spot A1, spot A2, etc.) that result in "acceptable" spectra during data acquisition and to do this until several hundred thousand spectra have been added to the sum buffer. Summing up/averaging several hundred thousand spectra increases the signal to noise ratio, and therefore allows for the detection of significantly more peaks, as described previously.

As is the case with non-contiguous raster scanning described above, the use of grids as described in this section works best when the sample/matrix mixture is substantially evenly and homogeneously distributed over the entire spot, as shown in FIG. 3. A presently preferred method for achieving this is described later in this document for dilute-and-shoot serum and sinapinic acid (matrix). Because of this even distribution, we can therefore acquire spectra from virtually all locations/rasters on the sample spot, which eliminates the need for a precursory evaluation of all locations/rasters for "acceptable" spectra.

Figure 6:
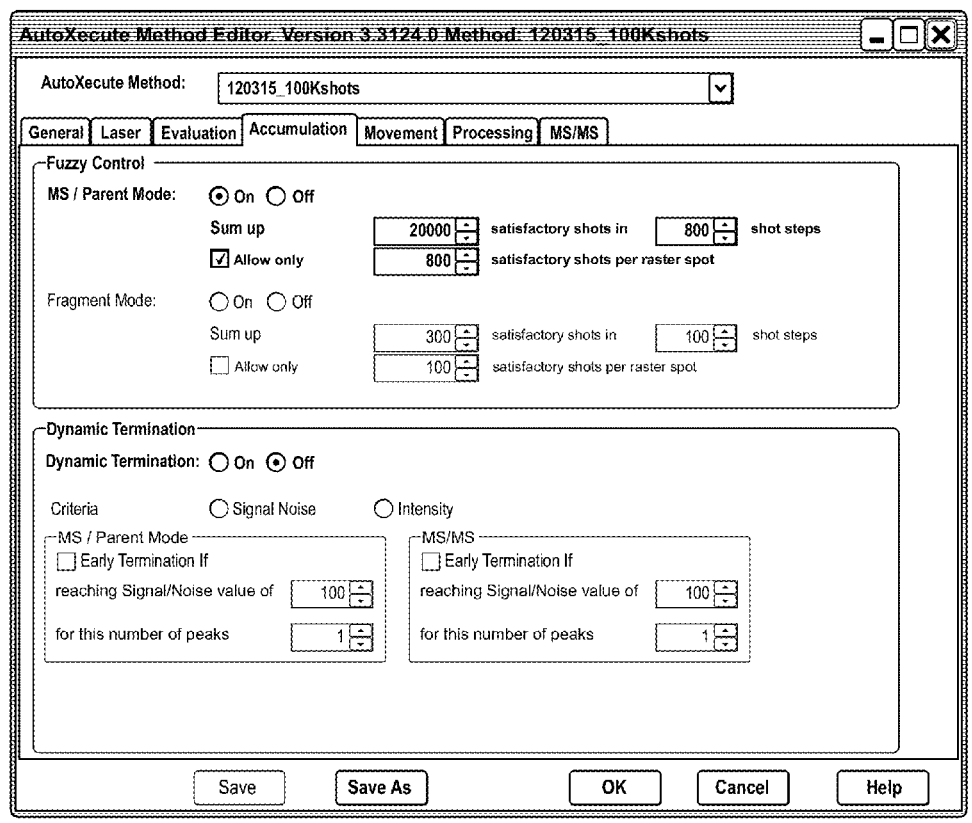
FIG. 6 is a screen shot from a MALDI-TOF instrument user interface showing commands for summing accumulated spectra from 800 laser shots per location/raster, e.g., in the raster scanning of FIG. 2B or 5.

Collecting several hundred thousand spectra on a sample spot can be achieved by defining a grid (FIG. 2B) that subdivides the spot 14 into sub-spots or grid elements 18, that covers the sample spot, and collecting a defined number of spectra from each location/grid point/raster within each sub-spot 18 until the desired number of spectra have been added to the sum buffer. Previous versions of the Bruker software only allowed for the summation of a maximum of 20,000 total spectra per sample spot in automatic mode (FIG. 6.)

To circumvent this limitation we initially defined a 5 by 5 grid area (FIG. 2B, 16) that divides each sample spot into twenty-five 8×8 grids or sub-spots 18 (FIG. 2B). A separate raster file is generated for each grid or sub-spot 18. The instrument is instructed to acquire 800 spectra (shots) at each location/raster within a grid 18 until 20,000 spectra have been added to the (spectrum) sum buffer. At that time, the automatic method 1 instructs the instrument to move to the next grid or sub-spot 18 and use the next raster file and generate another 20,000 spectra. In practice, one designs 25 raster files, one for each sub-spot 18, each of which is attached to a separate autoExecute™ (Bruker) method that acquires data according to evaluation criteria setup within the method.

This procedure permits acquisition of 500,000 shot spectra (20,000 shot spectra per grid x 25 grids) in batches of 20,000 shots each using Bruker's Flexcontrol™ software tools without having to use imaging applications such as flexImagmg™ (Bruker). The result of this procedure is 25 spectra files for one sample spot each containing one summed spectrum composed of 20,000 shot spectra. These 25 spectra files can then be summed to produce an overall spectrum for a single spot on a MALDI plate obtained from 500,000 shots, e.g., as shown in FIGS. 1C, 1D and 1E.

The most recent version of Flexcontrol™ (Bruker) allows one to accumulate a summed spectra from up to 500,000 shots. For example, in FIG. 6 the autoExecute™ (Bruker) method editor allows the summation of 20,000 shots in 800 shot steps (800 shots per location/raster).

However, one can only collect one summed spectra (sum of x transient spectra) per sample spot. To acquire several batches of summed spectra from a single sample spot, we had to make adjustments to existing software features in the MS instrument. With these adjustments we can acquire spectra from one or several rasters that makes up a grid such as the ones described above, and save each transient or location spectrum individually. For instance, the instrument can be instructed to collect and save each 800 shot location spectra acquired at each raster (x,y position) in the grid or sub-spot 18 in FIG. 2B without having to add to the sum buffer. The same process is repeated for all the sub-spots within the sample spots A1, A2, A3 etc. (e.g. 800 shot spectra can be acquired from 250 rasters per sample spot=200,000 shots per sample spot). The location spectra can be acquired with or without applying spectrum filtering in autoExecute™ (Bruker).

C. Image Analysis

One option for automation of spectral acquisition is image processing techniques to identify spatial locations on a spot with high protein yield/high sample concentration particularly in the situation where the sample is not spatially evenly distributed over the spot and instead is concentrated in discrete areas. In one possible embodiment, the camera included in the instrument is used to acquire an optical image of a training spot. Then, mass spectra are acquired from a raster of locations on the training spot. Resulting mass spectra are used, in combination with the optical image of the spot, to generate a classification mechanism to detect, from the optical image, high yield locations of further spots prepared from a given sample preparation. This classification would then be applied to the actual sample spots. While this is an elegant solution, we encountered issues with capturing the camera feed, and the repeatable calibration of locations from camera images to laser shot locations.

An alternative method is to investigate a spot using the mass spectrometer directly in the form of a mass spectral imaging approach. The idea is to first run a preliminary scan and shoot a low number of shots (dozens) at each location of a fine scale (square) pattern on a spot. Spectra will be collected for each of these raster locations, and the total ion current, or ion current within some predefined range of m/z, will be recorded for each location. A new raster file will be generated based on the N highest intensity locations from the preliminary scan run, and used in the final acquisition of mass spectra. This approach utilizes the Bruker FlexImaging™ software as the most feasible solution to generate multiple spectra in the mass spec imaging run. Software analyzes these spectra, and generates a final raster scan pattern. While this method will likely be useful for standard dilute and shoot processes using sinapinic acid as a matrix, it might be suboptimal for other matrices and for pre-fractionated sample sets (e.g. CLCCA, see Leszyk, J. D. Evaluation of the new MALDI Matrix 4-Chloro-α-Cyanocinnamic Acid, J. Biomolecular Techniques, 21:81-91 (2010)), and other methods like NOG precipitation (Zhang N. et al., Effects of common surfactants on protein digestion and matrix-assisted laser desorption/ionization mass spectrometric analysis of the digested peptides using two-layer sample preparation. Rapid Commun. Mass Spectrom. 18:889-896 (2004)). An important aspect of this alternative method is to find acquisition settings in the MS imaging part so as to not generate too large files. A standard acquisition file is of the order of one megabyte, and for a 400 by 400 raster scan (400 locations, 400 shots per location) we generate 16,000 spectra. As the requirements for these spectra are not onerous at all, and we only need to estimate the total ion current, we can work with low resolution settings. It may be possible to directly obtain a list of usable locations from automatic spectral acquisition settings, i.e. getting a list of successful or failed acquisitions. From our investigations it appears that it may be possible to use mass filtering as part of the MS imaging package to generate a list of locations (recognized via a file list) that pass certain criteria. While this will greatly help with the generation of a prototype workflow, it will need to be optimized via specialized software to avoid a semi-manual process.

Figure 7:
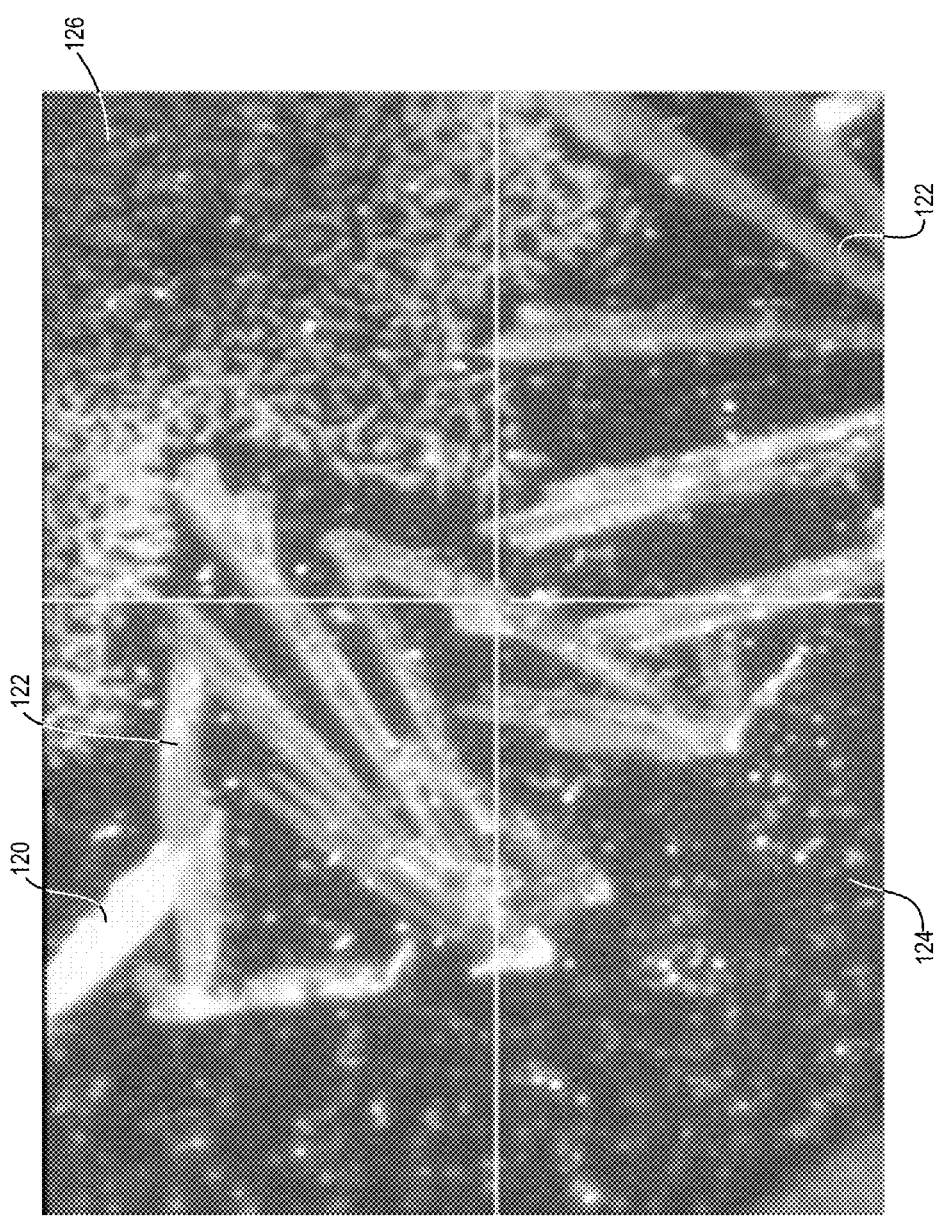
FIG. 7 is an image of a portion of a sample spot showing areas where the sample/matrix mixture does not crystallize in a spatially uniform manner.

FIG. 7 shows a region of a MALDI spot using CLCCA as a matrix, where the high yield areas consist of linear structures and areas of low yield are shown as dark areas. For these cases, where the matrix sample crystallizes very unevenly, like shown in FIG. 7, the image analysis approach seems most sensible. The image analysis identifies the relatively high yield areas (120, 122). The relatively low yield areas, such as the areas 124 on the lower left and the matrix area 126 are identified by the image analysis software and are ignored during shooting.

The image analysis software to identify high and low yield areas on a spot could take a variety of forms, and can be developed by persons skilled in the art. For example, the black and white image of the spot (FIG. 7) consists of an array of pixels, each having an 8 bit quantized value, with 0 being black (no signal) and 255 being white (saturated). The filtering can be used to identify areas of relatively high yield, such as by identifying pixels with a pixel value greater than say 100 being identified as "high yield" and pixels having a pixel value lower than 40 being identified as relatively "low yield". The scanning then proceeds to those areas of the sample spot in which the corresponding pixel has a value of 100 or more. It may also be possible to filter out spot locations in which the pixel value is 240-255 as such areas may be determined to have salt crystals or other properties that result in low yield. Referring again to FIG. 7, the pixels for the crystalline structures 120,122 have pixel values falling in the range of 100-240 and thus would be scanned whereas the black areas 124 and 126 would not be. Morphological processing techniques could also be used to identify structures such as the crystals 120 of FIG. 7. The image analysis software could include both morphological processing and filtering to determine areas to scan. Additionally, the spot can change during the course of scanning (due to depletion of the sample) and the image processing can be run during the scanning to optimize the shooting over the course of generating 100,000 or more shots from a spot, and those locations of low sample concentration avoided during shooting.

Figure 8:
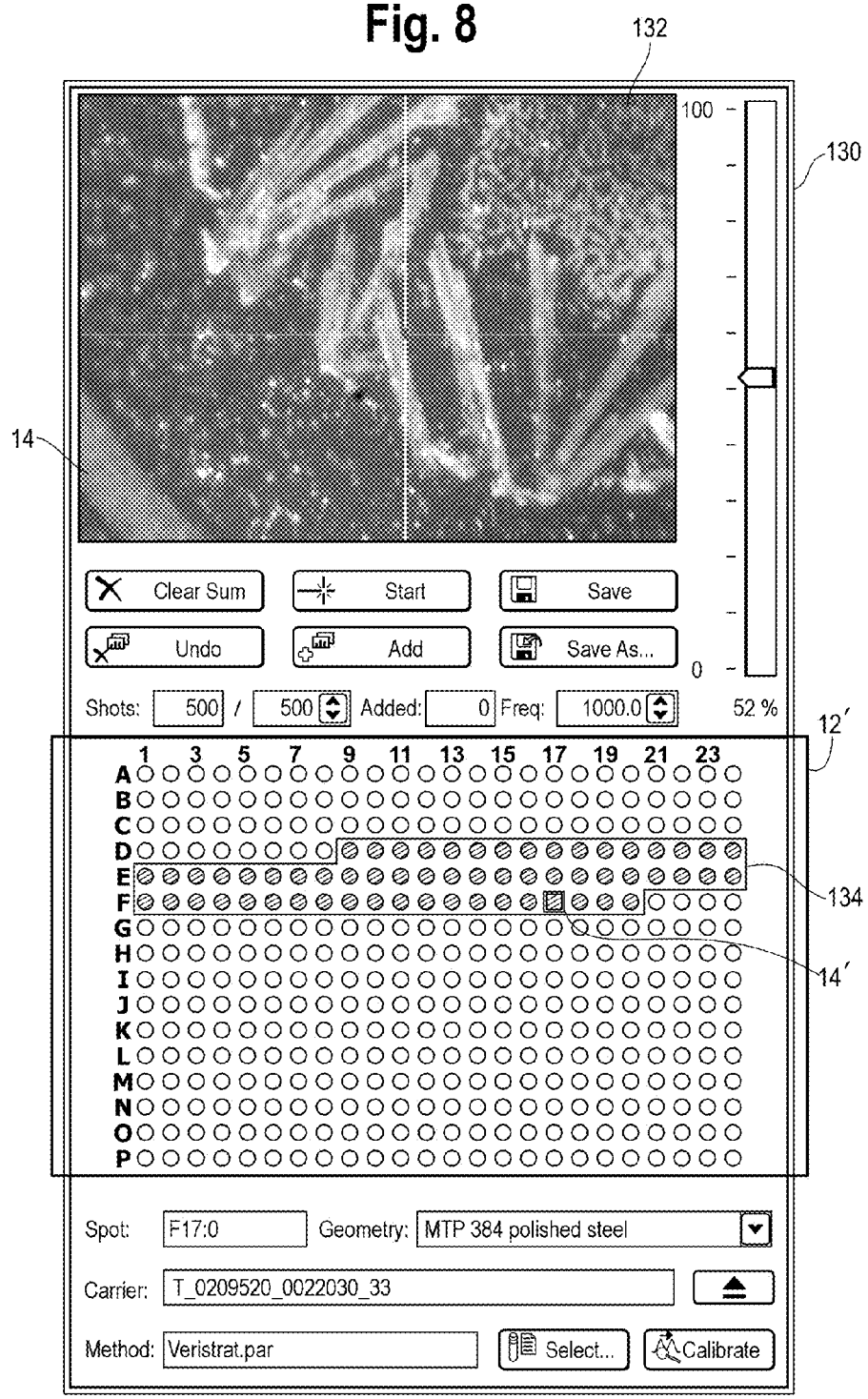
FIG. 8 is a screen shot from a MALDI-TOF instrument user interface showing an image of a portion of a spot captured by a camera in the instrument, and the selection of a group of spots for automated raster scanning of the spots.

FIG. 8 is a screen shot from a MALDI-TOF instrument showing the display of the instrument workstation 130, including an image 132 of a spot 14, in this case spot F17 of the plate. The layout of the plate is shown at 12', with the spot F17 indicated at 14'. A group of spots 134 (D9 to F20) are selected for running in an automatic mode using the image analysis method described above.

Figure 9:
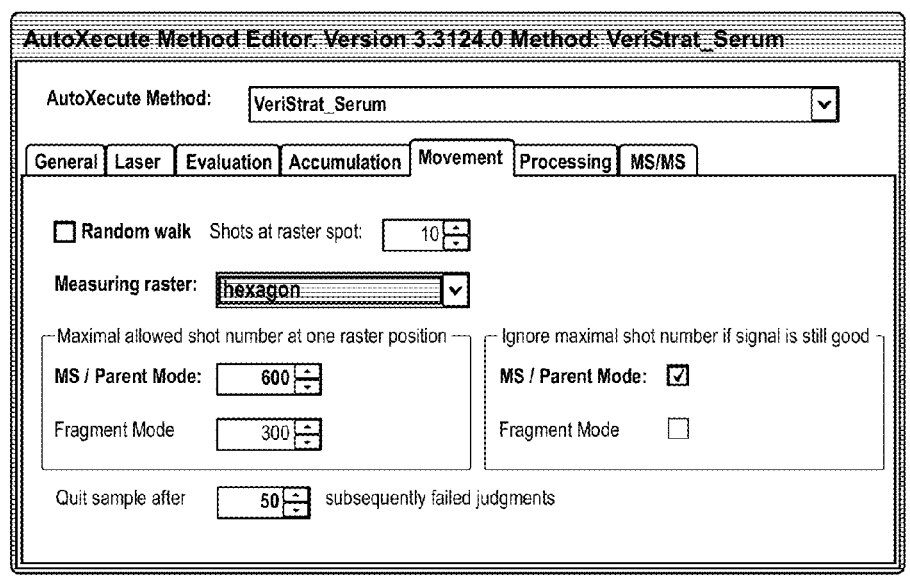
FIG. 9 is another screen shot from a MALDI-TOF instrument user interface showing tools for evaluation of spectra, accumulation of spectra, and movement of a laser across a spot for firing in different patterns.

FIG. 9 is another screen shot from the instrument. Current instruments allow the user to set evaluation regions to accept or reject transient spectra (using the Evaluation tab), set how many spectra to accumulate per spot (using the Accumulation tab) and "move" across the spot so that the laser can fire in a certain pattern (using the "Movement" tab, shown). The options include random walk or movement in pattern, e.g., hexagon or spiral. The software also allows the user to keep firing the laser and acquiring and adding to the total spectra according to such parameters until spectra from 750 shots are collected from a shot location, and then move to the next shot location. One can set the number of tries before the shot location is considered a failed spot. The image analysis methods in which likely areas of low yield are identified, and shooting in those areas avoided, helps in considerably reducing or eliminating those failed judgments.

Figure 10:
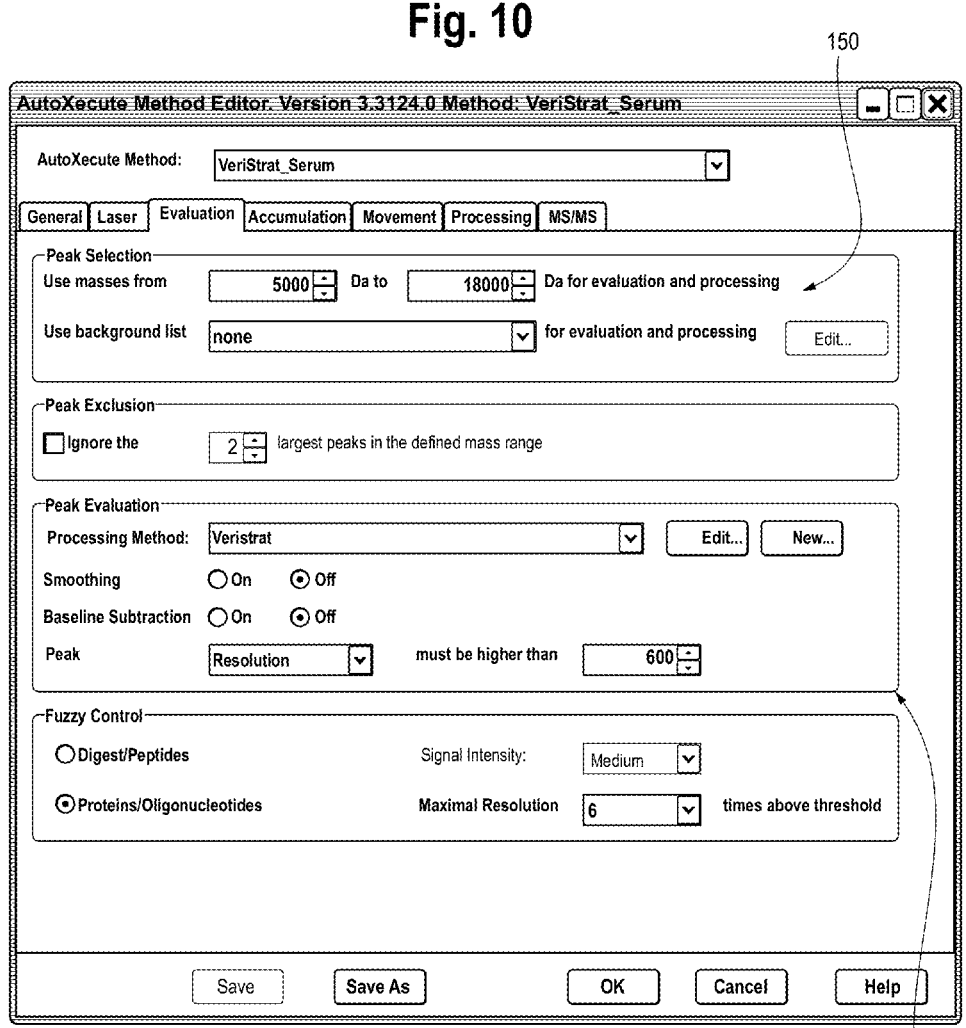
FIG. 10 is a screen shot of an evaluation page for accepting or rejecting transient spectra during data acquisition.

FIG. 10 shows an evaluation page where a mass range for accepting or rejecting transient spectra is selected, as indicated at 150. During acquisition, if a transient spectra does not have peaks in the predefined range—in this case 5,000 to 18,000 Da, that pass the threshold set (based on resolution, signal intensity or other factors), then it will be rejected. That is, the transient spectra will not be added to the sum buffer to form the location spectrum (summing the spectra from all of the shots).

Figure 11:
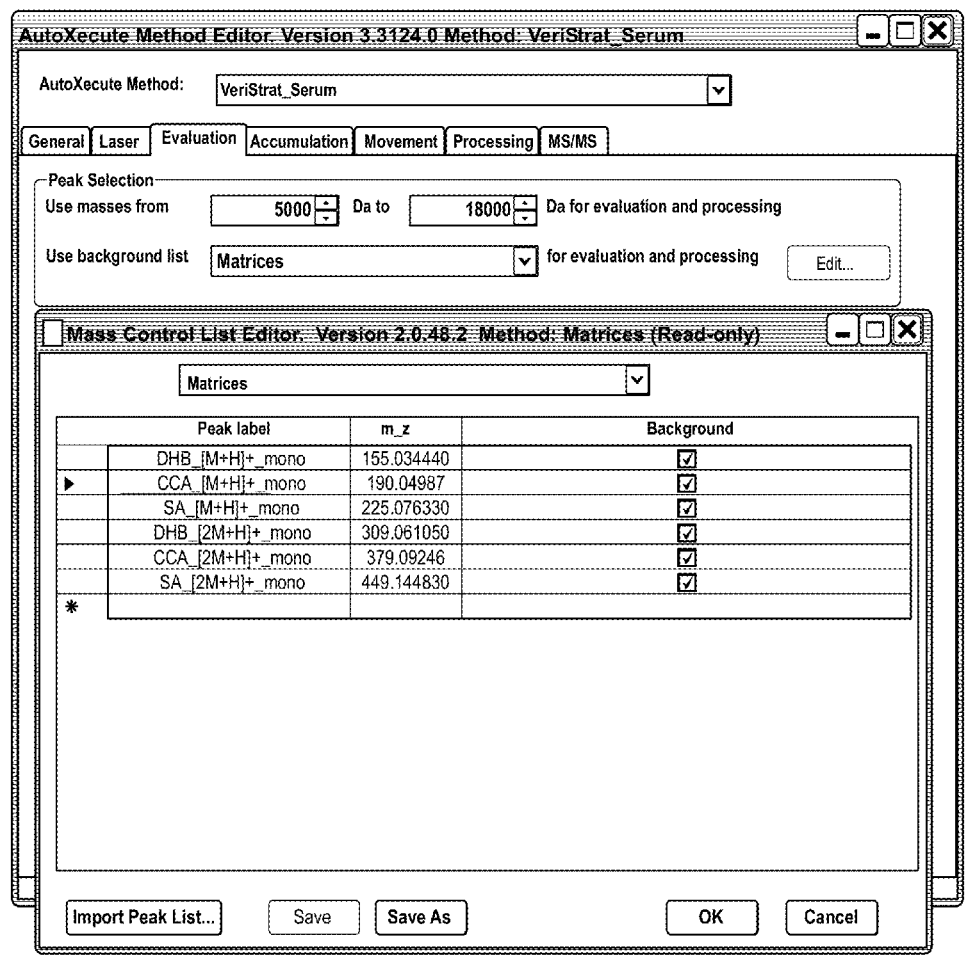
FIG. 11 is a screen shot showing exclusion lists for eliminating background peaks.

FIG. 11 shows an evaluation page where if there are specific peaks that one does not want included in the evaluation one can make an exclusion list and tag these peaks as "background peaks." The software has predefined "control lists" for matrices which define background peaks, or one can import a peak list.

3. Collection of Spectra from Multiple Spots

In general, one can extend the deep-MALDI technique to combining spectra from multiple spots. For example, one can obtain 500,000 shots of a sample from each of the spots A1, A2, A3, A4 and A5 on a standard MALDI plate (See FIG. 2A), and combine (sum) the resulting spectra into one overall spectrum consisting of a sum of 2,500,000 spectra (shots). A priori, there is no reason to believe that one could not combine spectra from multiple spots to reach extremely high number of shots, i.e., 100 spots×1 million shots each could give us results from 100 million shots. There may be practical limits to this procedure, e.g., the laser may fail too often.

Example

In one example of this method, it is possible to collect spectra from 5 million shots from multiple spots of the same serum on a MALDI plate, using manually or automatically generated rasters for scanning the multiple spots using the techniques described previously. In this method, it is preferred to obtain reproducibly homogenous spots of a single sample on the MALDI plate. This can be achieved using the methods described herein.

1. Spotting Diluted Serum onto MALDI Target Plate.
Procedure:
Dilute serum 1:10 with HPLC grade water and vortex. Mix sample with matrix (20 mg/ml sinapinic acid in 50% ACN/ 0.1% TFA) 1:1 (v/v) in a 0.5 ml microfuge tube and vortex. Spot 4 µl of the matrix/sample mixture onto one or more spots on the MALDI target.
Thirty six spots (locations) in the MALDI plate were used in this example:
Tube 1: spotted on locations E13, E14, and E15 of MALDI plate (See FIG. 2A)
Tube 2: spotted on locations E16, E17, and E18
Tube 3: spotted on locations E19, E20, and E21

Tube 4: spotted on locations E22, E23, and E24
Tube 5: spotted on locations F1, F2, and F3
Tube 6: spotted on locations F4, F5, and F6
Tube 7: spotted on locations F7, F8, and F9
Tube 8: spotted on locations F10, F11, and F12
Tube 9: spotted on locations F13, F14, and F15
Tube 10: spotted on locations F16, F17, and F18
Tube 11: spotted on locations F19, F20, and F21
Tube 12: spotted on locations F22, F23, and F24
Sample spots E13 to F18 (Tubes 1-10) were directly applied after vortexing using the same pipette tip 3 times (3×4 ul of 15 µl in each tube; while the last six samples spots F19-F24 (Tubes 11 and 12) were applied as in spots E13-F18, but also pipetted up and down on plate.
Spots on MALDI plate were allowed to dry at ambient temperature by placing target plate on bench-top.

Result:

For spots E13 to F17 (which were directly applied to plate with no further on-plate mixing) the third spot from each tube was clearly more homogenous than the first two. Homogeneity was assessed visually: third spot is best, second spot is second best, first spot is the least homogenous, with the exception of E23 which is from second of three spots from tube 4, but looked more like the third spotting from each tube than the second spottings.

Sample spots F18, F19, F20, F21, F23 and F24, which were mixed by vortexing in tube and pipetted up and down on plate, were fairly similar and had the same uniform appearance as the third spot in the set from E13 to F17. F22 looked about the same as E23.

2. Acquisition of Spectrum from 5 Million Shots

Mass spectral data from approximately 312,500 shots per spot was obtained from sixteen MALDI spots after the above procedure was performed:
E15, E18, E21, E23, E24, F3, F6, F9, F12, F15, F18, F19, F20, F21, F23 and F24.
Using raster scanning files as described above and in the Appendix, the spectra from the each of the spots was summed to produce an overall spectra of the sample obtained from approximately 5,000,000 shots.

4. Optimization of Sample Application to MALDI Plate (Spotting)

The sample application to the MALDI plate is optimized to provide homogenous and even distribution of the crystallized sample to each sample spot on a MALDI plate, an example of which is shown in FIG. 3. Several experiments were performed as described below to find an optimum procedure for supplying the sample mixture to a spot on the MALDI plate ("spotting"). These experiments are described in this section.

Initially, several different preparations with serum were prepared. 2 µl of matrix was spotted unless otherwise noted. Diluted sample and matrix medium were mixed in a sample prep tube unless otherwise noted. We did not spot more than 1 spot from a single prep tube unless otherwise noted as taking multiple aliquots out of the sample prep tube affects crystallization.

Ground Steel Plate experiments were conducted which produced homogeneous spots. The procedures were as follows:

1. Diluted sample 1:10 (2 µl sample+18 µl of water), then mixed 1:1 (v/v) with matrix (sinapinic acid 25 mg/ml) in 50% ACN/0.1% TFA and spotted 2 µl of matrix. This procedure did not produce good, homogeneous crystals.

2. Primed matrix tip. Pipetted 2 µl of matrix into spotting tip and let it sit for 30 seconds. Diluted sample 1:10 (2 µl sample+18 µl of water), then mixed 1:1 (v/v) with matrix (sinapinic acid 25 mg/ml) in 50% ACN/0.1% TFA. Ejected excess matrix from pipette tip. Placed pipette tip in sample matrix mixture and pipetted up and down 3 times. Spotted 2 µl of sample matrix mixture without changing the tip. This procedure formed good crystals that were homogeneous. Because this is a ground steel plate the sample matrix mixture doesn't spread out as much as on the polished steel plate. The dried crystals that are left in the pipette tip might improve crystallization by acting as a seed for further crystal formation.

3. The effect of temperature on crystallization was studied. Diluted sample 1:10 (2 µl sample+18 µl of water), then mixed 1:1 (v/v) with matrix (sinapinic acid 25 mg/ml) in 50% ACN/ 0.1% TFA. Place sample in 37° C. water bath for 5 minutes. Removed sample from water bath and spotted immediately. This procedure did not produce good, homogeneous crystals.

4. Repeated experiment 2. above, but spotted 4 µl of sample mixture instead of 2 µl. This procedure formed good crystals that were homogeneous. Spotting 4 µl fully covered the spot diameter and produce good crystals and data. This is the procedure currently considered optimal.

Comment: The procedures for spotting here are offered by way of example and not limitation, and variation from the disclosed methods are of course possible. For example, one may mix the matrix and sample material in the tube and let it set for several minutes before spotting. It has been noted that one gets more homogeneous crystals the more spots are made from the same tube using the same pipette tip. For example, one could spot 10 spots from the same tube using the same tip and only collect data on the last 5 or so spots; or alternatively one could discard the first five 4 µl aliquots from the tube before commencing spotting on a MALDI plate.

We have also found that following the procedure in 1 but using the same pipette tip to spot the same sample tube 10 times (2.5 µl per spot) onto a polished steel target plate yields similar results (spectral quality).

5. Analytical Performance Evaluation

Technical Reproducibility

Technical reproducibility studies can be done, e.g. to run 1,000 technical replicates in batches of 100 each day. One can study dependence on sample (spot) preparations (on or off plate), in particular to see whether there are preparation methods that yield more uniform ion-current yields, e.g. variations in sample dilution. One can also monitor how the number of high-yield locations changes from spot to spot, and how to minimize variations in this. Monitoring and logging all acquisitions and preparations at a high level of granularity is good practice.

Sample to Sample Reproducibility

Similar issues of sample to sample reproducibility can be studied with respect to sample to sample variations. New phenomena might occur: It may be that some samples are protein rich, and result in spots with more high-yield locations. It may be possible to obtain measures from some manner of sample attributes (optical density and color), or standardize sample acquisition devices (e.g., for serum) to generate more reproducible procedures. One may use a combined sample set with as heterogeneous a source as possible to attempt to cover most variations. Such a set should be obtained from studying existing sets and matching according to known sample collection and conditions, which makes strong use of existing sample databases.

Sensitivity

Observing more peaks in the spectra raises the question what abundance range we can see in this method, and what protein types are actually visible. This deals with the 'conventional wisdom' that in MALDI MS of complex samples one cannot observe lower abundance ions due to 'ion suppression', the idea that ions from more abundant proteins suppress the ion signal from less abundant proteins, therefore rendering the less abundant proteins undetectable. This idea appears to be solely based on the lack of observation of lower abundance ions. Indeed, our observation of an increase in peak content (see e.g., FIG. 1C) casts some doubt over this interpretation. Rather, it appears that one has to take seriously the (semi)quantitative nature of MALDI MS. If one agrees that protein abundance spans a wide range over many orders of magnitude, then one would expect that corresponding mass spectra would mimic this behavior by exhibiting a vast difference in peak height (or rather the area under a peak). One would not expect to observe low abundance proteins in MALDI spectra, not because they do not ionize, but rather because the amplitude of peaks corresponding to low abundance proteins should be very low. As it is common practice in mass spectrometry to focus on large peaks, and because lower abundance peaks would be orders of magnitude smaller, it is not surprising that these peaks have not been observed before. This is not to say that phenomena like ion suppression do not occur, or that ionization probability does not play a role, but to say that these phenomena do not entirely suppress peaks originating from low-abundance proteins, and that, if one looks for low abundance protein peaks in the low intensity region of spectra, they do indeed become observable. The quest for covering a significant percentage of the serum proteome can thus be viewed as a quest for extending the dynamic range of mass spectra. As with any other counting-based technique the simple solution to this problem is to increase statistics by increasing the number of detected ions (per time-of-flight bin).

In order to get more confidence in this simple interpretation, which runs counter to conventional wisdom, one may wish to establish the dynamic range of mass spectra and link it to abundance of proteins. This should be done both from an analytical chemistry point of view, establishing sensitivity curves (as a function of m/z), as well as through the identification of proteins corresponding to some peaks and comparative abundance measurements of these proteins via orthogonal techniques like ELISAs.

Analytical Sensitivity Via Spiking Experiments

The idea is to spike varying concentrations of characterized proteins into a serum sample, see whether one can see the corresponding peaks, and decrease the concentration until the spike peaks disappear. One should choose protein standards spanning the mass range from 5 kDa to 30 kDa, ideally spaced in lkDa intervals. It may be necessary to compromise, but we should aim for some decently tight coverage of the interesting mass range. We can be less rigorous at higher masses. A control experiment could be performed where the protein standards are reconstituted in water, to evaluate what effect the presence of serum has. One can graph peak intensity versus abundance as a function of the number of shots. This should give us an idea of the dynamic range of the method. One can also generate sensitivity curves as a function of m/z depicting the lowest concentration at which the spikes are observable (parameterized by S/N cut-off) for different numbers of shots.

Using Pre-Fractionated Samples

The methods of this disclosure can be used in combination with precipitation methods for fractionating a sample, e.g. NOG precipitation, de-lipidifying, and so on. The methods can also be used with other matrices like CLCCA. It is likely that these methods could also benefit greatly from the deep-MALDI approach. Our preliminary data using sample pre-fractionation indicate that one does indeed see different peaks, but the peak content was far from optimal. This might be expected as one purpose is to get rid of high abundance proteins.

In the past we attempted to use depletion and/or mass filtering to reduce the content of unwanted proteins like albumin and hemoglobin, but none of these methods led to a total removal, and remnants of these peaks were still visible. Using the deep-MALDI approach described here on depleted or mass filtered samples should yield better results, as reducing large peaks will also reduce the dynamic range necessary to see lower abundance proteins.

6. Further Considerations a. Obtain Sensible Choices of Spectral Acquisition Settings In the autoExecute™ (Bruker) method, it is possible to define filtering settings in order to only collect transient spectra that pass certain criteria; in our case we want to only add those transient spectra (arising from <xx> number of shots) that have a total ion current larger than an externally defined threshold. While this does not seem possible in a simple manner, there are filter criteria in the processing method tab that might be used for similar purposes. Alternatively, there might be parameters in the peak evaluation methods that we could tune for this purpose. While this will not reduce the number of shots, it may overcome the problem of shot bias towards earlier shots, i.e. not to acquire transients consisting only of noise. The use of automated filtering operations in summing transient spectra to generate location spectra avoids the problem of bias.

b. Use standard methods to evaluate spectra, e.g., pre-processing, background subtraction, alignment and so forth. See the U.S. Pat. No. 7,736,905, incorporated by reference herein.

c. Optimization of Spectral Acquisition Parameters Beyond Spectral Filtering:

The optimal number of laser shots per location.
The optimal laser power (and the definition of this via a standard).
The optimal number of locations on a one spot that can be reliably probed.
The mass range should the above be optimized to.
All of these parameters can be optimized.

d. Determining the Limits of Combining Spectra from Multiple Spots (See Above Discussion)

e. Improvement in Resolution.

When many more peaks surface from the sea of noise (compare FIG. 1C to FIG. 1A) peaks will overlap so much making it difficult to resolve individual species in a reliable fashion. While it is unlikely that we will see multiple peaks in a given Dalton we should aim to have around 1-5 Da resolution over the m/z range of interest. This may require changing voltage and delayed extraction settings, as well as optimizing the data acquisition electronics. Of course if we make time-of-flight bin widths too small, this will lead to less detection events per time-of-flight bin, and hence higher noise levels in each bin. One needs to find a reasonable compromise between resolution and increase in bin counts (via multiple shots).

f. Assess Peak Content as a Function of the Number of Shots

1. Achievable Range of S/N Ratio (Amplitudes)

The principal idea of the deep-MALDI method is based on the simple observation that the absolute intensity of a time-of-flight bin comprised only of noise scales with the square root of the number of shots, whereas the absolute intensity of a TOF bin containing a signal should scale linearly with the number of shots (with some caveats). Hence, increasing the number of shots should lead to more events per TOF bin, and eventually even small peaks become distinguishable from noise. The number of ions detected is proportional to the area under a peak; under the assumption that for a given m/z range peaks have similar widths, and under the assumption that peaks are approximately Gaussian, the area under the peak is proportional to the height of a peak multiplied by a form factor that depends on the width of the peak at half maximum (Full Width at Half Maximum, FWHM). It would be helpful to have a standard curve (as a function of m/z) that relates peak amplitude to abundance in order to be able to achieve a given sensitivity, i.e., to correlate a number of shots to reveal a known peak at a given intensity level.

2. Peak Numbers as a Function of S/N Cut-Off; Better Definition of Peaks

The simplest idea to measure peak content is to measure the number of detected peaks as a function of S/N cut-off; preliminary experimentation with this approach does not give the expected behavior, mainly for small S/N cut-offs. This may be caused by an oversensitivity of our peak detector at low S/N cut-offs (or issues with noise estimation). Some further evidence for this behavior is given by the observation that some detected peaks for smaller number of shots disappear for higher number of shots. Maybe the number of events in the relevant TOF bins is too small for the noise estimator to work well for smaller number of shots. From looking at the spectra (see FIG. 1) it is clear that peaks are visually much better defined with more shots (100,000 or 500,000 shots, FIGS. 1B and 1C) than for fewer shots (FIG. 1A, 2,000 shots); it may be desirable to add additional criteria for peak definitions to render this evaluation more quantitative.

g. Measure Reproducibility of the Method

The technical reproducibility of the deep-MALDI method can be measured, i.e. to compare deep-MALDI spectra from technical replicates (multiple spots of the same sample) as a function of the number of shots. This should be measured by overlaying coefficient of variation (CV) vs. amplitude curves, ideally for the same peaks. In a first pass 100 technical replicates should be sufficient for a preliminary determination of technical reproducibility. One can also measure CVs for determination of m/z of individual peaks to get a measure of the achievable mass accuracy. This should be done with and without spectral alignment.

Having deep-MALDI spectra from 100 technical replicates enables further analysis: We can combine groups of ten replicates, and again measure peak content and reproducibility. Combining all technical replicates should in principle generate a spectrum similar to one obtained from 100 times the individual number of shots per spot.

h. Discovery of Common Peaks Across Samples

Having established technical reproducibility, one can investigate the variation in peak content arising from different serum (or other) samples. One can evaluate sample-to-sample (STS) reproducibility to discover peaks that are common across subjects. It is likely advantageous to work with an unbiased sample set containing 'healthy' subjects to discover the common peaks. Two options are obvious: An early diagnostic set, e.g. one of the prostate sets that do not show much in standard dilute and shoot settings, and a mixture of 'healthy' controls with a variety of cancer cases. Analysis needs to define the most suitable set with a size of ~100 samples.

i. Alignment, Normalization, and Peak Definition

One use of the inventive methods is to discover and list common peaks using deep-MALDI spectra. The peak content will be evaluated using CV vs. amplitude curves, ideally as a function of shot number (or any other suitable measure, e.g., number of events per TOF bin, . . . ). This work may also lead to a set of alignment peaks. In the same fashion one may wish to evaluate various normalization procedures. As we now have many more peaks spread over the whole observable m/z range, it is unlikely that there are large enough uninformative regions to facilitate region-based normalization. Rather, one can develop peak-based partial ion current (PIC) normalization. This requires the identification of stable (both in position and amplitude) peaks present in serum. As the process for this is somewhat arbitrary due to a lack of a stopping criterion in the algorithm it would be advantageous to predefine such a list of peaks, analogous to a list of pre-defined peaks used in spectral alignment.

An additional use of the inventive method is in biomarker discovery, but with much larger feature sets than we are currently using. Since the feature sets are much larger, this may lead to better performance of some parts of the algorithms, e.g. the estimation of false discovery rates. The better peak definitions obtainable from deep-MALDI spectra may lead to better discrimination between informative and noisy features. However, having more features renders the feature selection problem more cumbersome, and emphasizes the need for feature pre-filtering.

j. Increase the Size of a Maldi Spot

Given the limitations arising from the size of the laser illumination as well as from the minimal grid size for the pre-rastering step, it may well be that there are not enough shot locations with sufficient ion-yield on a standard spot. A simple way to address this would be to increase the spot size. The FlexImaging™ (Bruker) software would support this very easily. There are also options of rectangular spotting areas used in MS imaging application that might be suitable for this purpose. An additional benefit of using larger spots would be that one does not have to worry whether one can locate a similar number of decent shot locations and generate spectra of similar quality from spot to spot. Sample volume does not appear to present an issue. If larger spots are possible, it would reduce the logistics to deal with multiple spots for the same acquisition, which may be necessary for high numbers of shots.

Appendix

This appendix describes a method of generation of 25 raster files with non-contiguous x,y coordinates. The steps make reference to tools provided with Bruker mass spectrometry instruments, but the methods are sufficiently general such that they could apply to instruments of other manufacturers.

The following steps were used to create a 25 cell grid—based on hexagon pattern:

1) Open Bruker's raster file "hexagon.raster" in notepad. This pattern has 889 coordinate points distributed over a MALDI target sample spot.
2) Remove points around the edges and reduced number of coordinate points from 889 to 750 from hexagon.raster and saved as "hexagon750.raster". See FIG. 2.
3) Divide the 750 x, y points into 25 batches of 30 x, y points that are saved as 25 separate raster files: "5×5_1.raster", "5×5_2.raster" . . . "5×5_25.raster". The files are named this way so the names will be the same as those that would be generated for a 25 cell grid had one used the sequence generator (see item 6 below). The result is similar to FIG. 4, above.
4) Copy 25 raster files ("5×5_1.raster", "5×5_2.raster" . . . "5×5_25.raster") to Methods\AutoXRasterFile.
5) Create AutoXecute method "120411_375shots.axe" in AutoXecute Method editor. New method ("120411_375shots.axe" is similar to "120315_100kshot.axes" except for total spectra accumulation and shots per location (Table 1).

TABLE 1

| AutoX method | S/N | Laser focus | Accumulation (shots per grid/cell) | Shots per raster spot |
|---|---|---|---|---|
| 120315__100kshots.axe | 8 | 4-large | 20,000 | 800 |
| 120411__375shots.axe | 8 | 4-large | 15,000 | 750 |

6) In order to "force" the sequence generator prototype to generate AutoX methods using the 25 rasters ("5×5__1.raster", "5×5__2.raster" . . . "5×5 25.raster") created as described above:
1. selected "square" for 'generation method' and cell and grid dimension values=5 for columns as well as rows (FIG. 4).
2. When prompted if you want to overwrite rasters, chose "No". Prompt pops up because we had predefined rasters with the same file names that would have been generated by the sequence generator ("5×5__1.raster", "5×5__2.raster" . . . "5×5 25.raster") already saved in the target folder (Methods\AutoXRasterFile).
7) Create AutoSequence file using sequence generator prototype version: 20120406.1.
(Illustrations for steps 1-7 are found in the priority provisional application and the interested reader is directed to such illustrations).

Result of Testing New Rasters

We tried out the new noncontiguous rasters on two different spots and were able to acquire data with very few rejected spectra in 23 out of 25 and 24 of 25 cases for the first and second spot, respectively. Runs on both sample spots were done in under 10 minutes. In contrast, it took hours to collect the last set of ~248 k shots using our earlier square grids.

Using a rhomboid grid restricts the raster points to the center of sample spot where we generally see better signal. But when we used the rhomboid to generate a 25 cell grid we were able to collect data from only 8 out of 25 cells on a single sample spot. The total area on the sample spot covered with the new rasters is slightly bigger and there were a few overlapping rasters when grids were created using the rhomboid generation method of the sequence generator, but we think the key factor that accounts for the better results with the new rasters described above is the distance between consecutive locations that the laser hits.

The results we have so far indicate that our best option is to collect 250,000 shots per sample spot, and collect spectra on multiple replicates if more than 250 k shots are needed.

We can use 20 of the 25 raster files generated "manually" to collect 250,000 (20×12,500) to 300,000 (20×15,000) shots per sample spot.

We claim:

1. A method of analyzing a complex biological sample in the form of an unfractionated serum or plasma sample which has been applied to a sample spot on a MALDI-TOF sample plate using a MALDI-TOF mass spectrometer instrument, comprising the steps of:
    directing at least 100,000 laser shots to the sample at the sample spot in accordance with MALDI-TOF mass spectrometry; and
    collecting mass spectral data from the instrument;
    the method further comprising-the steps of:
    using image analysis of the sample plate to identify regions of relatively high or relatively low content of sample within the sample spot, and
    automatically controlling the direction of the at least 100,000 laser shots to the sample to regions of the sample spot having a relatively high content of sample.

2. A method of analyzing a complex biological sample in the form of an unfractionated serum or plasma sample which has been applied to a sample spot on a MALDI-TOF sample plate using a MALDI-TOF mass spectrometer instrument, comprising the steps of:
    directing at least 100,000 laser shots to the sample at the sample spot in accordance with MALDI-TOF mass spectrometry; and
    collecting mass spectral data from the instrument;
    wherein the method further comprising the steps of
    dividing the sample spot into a multitude of sub-spots without regard to the distribution of the sample in the spot;
    generating a raster file for each sub-spot, the raster file specifying of a multitude of discrete X/Y locations within the sub-spot for acquiring a mass spectrum from the sample using a plurality of shots;
    collecting a multitude of spectra at each X/Y location and summing the spectra to produce a summed spectrum for each sub-spot; and
    summing the summed spectra from each of the sub-spots to produce an overall mass spectrum of the sample.

3. The method of claim 2, further comprising the step of detecting one or more intact whole proteins in the unfractionated serum or plasma sample.

4. The method of claim 2, wherein the complex biological sample is obtained from a human patient with cancer.

5. A method of analyzing a complex biological sample in the form of an unfractionated serum or plasma sample which has been applied to a sample spot on a MALDI-TOF sample plate using a MALDI-TOF mass spectrometer instrument, comprising the steps of:
    directing at least 100,000 laser shots to the sample at the sample spot in accordance with MALDI-TOF mass spectrometry; and
    collecting mass spectral data from the instrument;
    the method further comprising the step of:
    defining a multitude of non-contiguous X/Y coordinates for raster scanning of the sample spot and then performing raster scanning of the sample spot, wherein during the raster scanning the sample spot is shot with a laser a multitude of times at each X/Y coordinate.

6. The method of claim 5, further comprising the step of defining a plurality of sets of non-contiguous X/Y coordinates for raster scanning of the sample spot and implementing a sequence of individual raster scans for the plurality of sets of non-contiguous X/Y coordinates.

7. A method of analyzing a complex biological sample in the form of an unfractionated serum or plasma sample which has been applied to a sample spot on a MALDI-TOF sample plate using a MALDI-TOF mass spectrometer instrument, comprising the steps of:
    directing at least 100,000 laser shots to the sample at the sample spot in accordance with MALDI-TOF mass spectrometry; and
    collecting mass spectral data from the instrument;
    the method further comprising the step of applying the sample to predetermined multiple sample spots arranged in an array on a MALDI-TOF plate, obtaining a mass spectrum from at least 100,000 laser shots applied to each of the multiple sample spots, and summing the mass spectra from each of the multiple spots to produce an overall mass spectrum for the sample.

8. The method of claim 7, wherein the obtaining step comprises obtaining a mass spectrum from at least 250,000 laser shots applied to each of the multiple sample spots.

9. The method of claim 7, wherein the mass spectra summed from each of the multiple sample spots consist of a mass spectrum obtained by applying between 1 and 10 million laser shots to the sample.

10. A method of acquiring a mass spectrum of a complex biological sample in the form of an unfractionated serum or plasma sample using a MALDI-TOF mass spectrometer, comprising the steps of:
automatically raster scanning the sample, the sample placed on a sample spot on a MALDI-TOF sample plate;
applying at least 100,000 laser shots to the sample spot during the automatic raster scanning in accordance with MALDI-TOF mass spectrometry, and
collecting mass spectra from the mass spectrometer from the at least 100,000 laser shots.

11. The method of claim 10, further comprising the steps of
subdividing the sample spot into a multitude of sub-spots without regard to the distribution of the sample in the sample spot; and
automatically raster scanning the sub-spots with a laser and obtaining at least 20,000 transient mass spectra per sub-spot; and
summing the transient spectra from each of the sub-spots to produce an overall mass spectrum for the spot.

12. The method of claim 10, wherein in the automatic raster scanning step the spot is raster scanned with the laser at least 10 times in at least 10 different raster patterns, each of which scans in discrete X/Y locations, and the collecting step collects spectra from at least 10,000 shots per each raster scan of the sample spot.

13. The method of claim 12, wherein the collecting step collects a spectrum for the sample spot from between 100,000 and 1 million shots applied to the sample spot.

14. The method of claim 10, further comprising the step of:
performing image analysis to identify one or more areas of relatively high concentration of sample within the sample spot and using such identification to automatically shooting the spot with a laser in such one or more areas.

15. The method of claim 10, further comprising the step of depositing the sample onto a spot on the MALDI-TOF sample plate in a homogeneous and spatially evenly distributed manner.

16. The method of claim 15, wherein the MALDI-TOF sample plate comprises a ground steel plate.

17. The method of claim 10, wherein the complex biological sample is obtained from a human patient with cancer.

18. A method of analysis of abundance of a molecule of interest present in an unfractionated plasma or serum sample by MALDI-TOF mass spectrometry, comprising the steps of:
a) doping the sample to a target abundance level of the molecule of interest;
b) applying the doped sample at the target abundance level to one or more sample spots of a MALDI-TOF sample plate;
c) conducting MALDI-TOF mass spectrometry by performing a number of laser shots on the one or more sample spots on the MALDI-TOF plate of at least 100,000 and generating a reference mass spectrum in which a peak corresponding to the molecule of interest is reliably present in the reference mass spectrum,
d) recording the number of shots and the intensity of the peak corresponding to the molecule of interest in the reference mass spectrum;
e) conducting mass spectrometry of an unfractionated plasma or serum sample of unknown concentration of the molecule of interest by subjecting the sample to MALDI-TOF mass spectrometry at the recorded number of shots and generating a resulting mass spectrum, and
f) comparing the peak intensity of the molecule of interest in the reference spectra to the peak intensity of the molecule of interest in the resulting mass spectrum to thereby determine the relative abundance of the molecule of interest in the sample of unknown concentration of the molecule of interest.

19. The method of claim 18, further comprising the step of performing steps a), b) and c) for two or more molecules of interest.

20. The method of claim 18, wherein the sample of unknown concentration is in the form of a unfractionated plasma or serum sample obtained from a human.

21. The method of claim 18, wherein the reference spectrum is obtained from two or more predetermined spots arranged in an array on the MALDI-TOF sample plate, each of the spots subject to at least 100,000 laser shots.

* * * * *